United States Patent
Amano et al.

[11] Patent Number: 6,162,185
[45] Date of Patent: Dec. 19, 2000

[54] TOUCH DETECTING DEVICE, TOUCH NOTIFYING DEVICE, INFORMATION INPUTTING DEVICE, TOUCH REPLICATING DEVICE, TOUCH TRANSMISSION SYSTEM, PULSE DIAGNOSTIC DEVICE, PULSE DIAGNOSIS TRAINING DEVICE, AND PULSE DIAGNOSTIC INFORMATION TRANSMISSION DEVICE

[75] Inventors: Kazuhiko Amano; Kazuo Uebaba, both of Yokohama; Hitoshi Ishiyama, Toride, all of Japan

[73] Assignee: Seiko Epson Corporation, Tokyo, Japan

[21] Appl. No.: 09/194,698
[22] PCT Filed: Mar. 27, 1998
[86] PCT No.: PCT/JP98/01396
  § 371 Date: Nov. 30, 1998
  § 102(e) Date: Nov. 30, 1998
[87] PCT Pub. No.: WO98/43538
  PCT Pub. Date: Oct. 8, 1998

[30] Foreign Application Priority Data

Mar. 28, 1997 [JP] Japan .................................. 9-078444

[51] Int. Cl.[7] .................................................. A61B 19/00
[52] U.S. Cl. ............................................ 600/557; 600/502
[58] Field of Search ........................ 600/587, 595, 600/557, 500, 504, 502, 501

[56] References Cited

U.S. PATENT DOCUMENTS 5,735,799 4/1998 Baba et al. .

FOREIGN PATENT DOCUMENTS

| 0 630 608 | 12/1994 | European Pat. Off. . |
| 4-348212 | 12/1992 | Japan . |
| 6-261870 | 9/1994 | Japan . |
| WO 94/15525 | 7/1994 | WIPO . |
| WO 94/15526 | 9/1994 | WIPO . |

*Primary Examiner*—Cary O'Connor
*Assistant Examiner*—Pamela Wingood

[57] ABSTRACT

The test subject attaches pulse wave detectors 1 to his fingertips, and presses down on pressure sensor 110. As a result, CPU 4 determines the DC component of the received light signal LS, and stores this in calibration table 50 in association with the pressure level. Subsequently, CPU 4 calculates threshold values, which can be used for grading the touch sensation, based on maximum value Pmax of the pressure level and calibration table 50, and stores this result in threshold table 51. When the subject grips an object with his fingers, the blood flow volume is detected by pulse wave detector 1 as received light signal LS. CPU 4 calculates the DC component of received light signal LS, compares this result to the threshold values stored in threshold value table 51, generates touch information SJ, and displays this on LCD 108. Accordingly, in this case, pulse diagnosis can be easily performed by expressing the degree of pressure in the pulse diagnosis as touch information SJ.

35 Claims, 16 Drawing Sheets

$Iout/Iin = 1-kC\Delta L$ k: ABSORPTION COEFFICIENT
L: LIGHT PATH

DIAGRAM SHOWING
LAMBERT-BEER RULE $Iout/Iin = (1-kC\Delta L)^5$ k: ABSORPTION COEFFICIENT
L: LIGHT PATH

DIAGRAM SHOWING
LAMBERT-BEER RULE $I_4$: COMPONENT OF LIGHT ABSORBED BY ARTERIAL BLOOD $I_3$: COMPONENT OF LIGHT ABSORBED BY VENOUS BLOOD $I_2$: COMPONENT OF LIGHT ABSORBED BY TISSUES

● : SUNN
▲ : KANN
■ : SYAKU

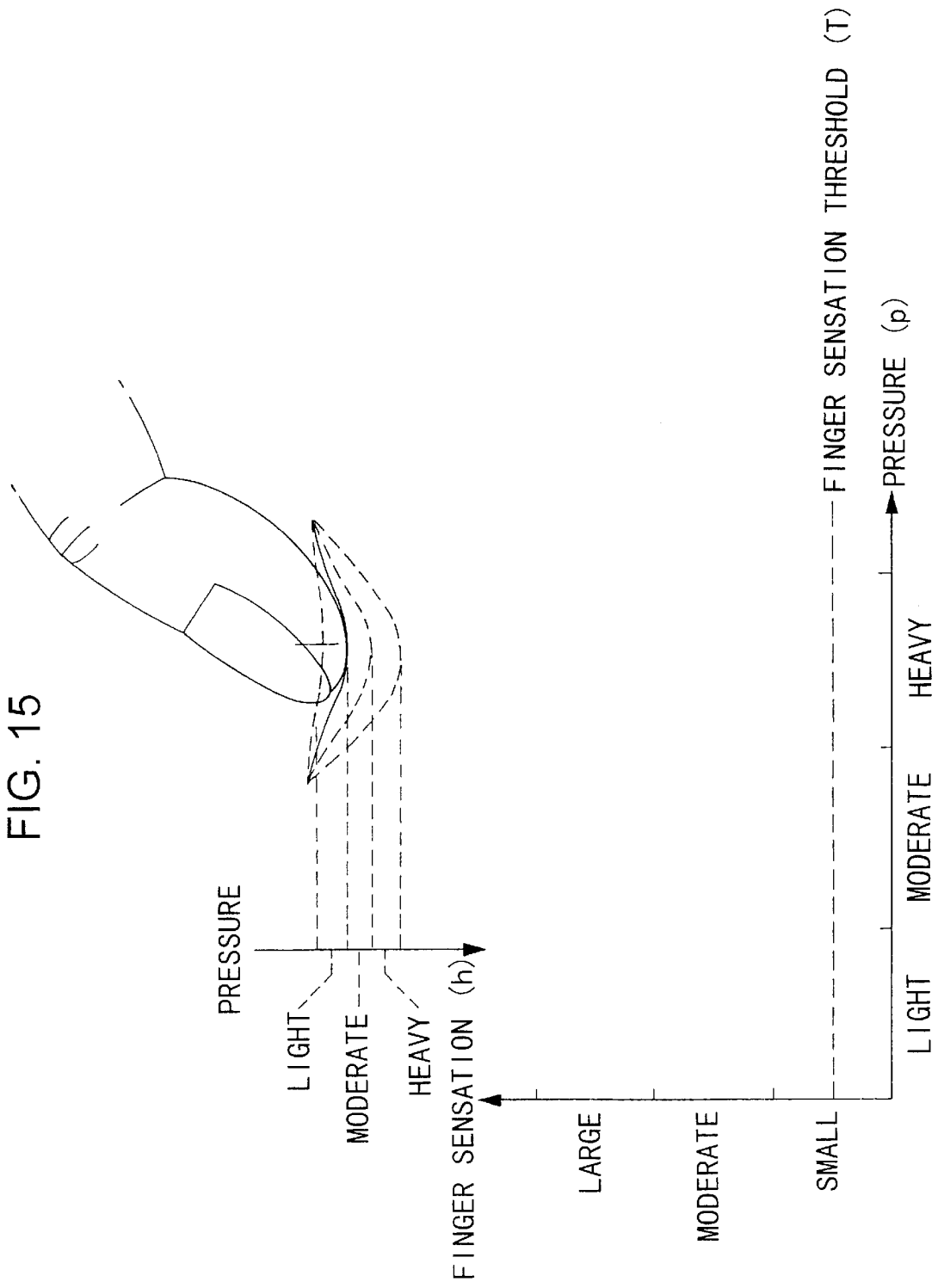

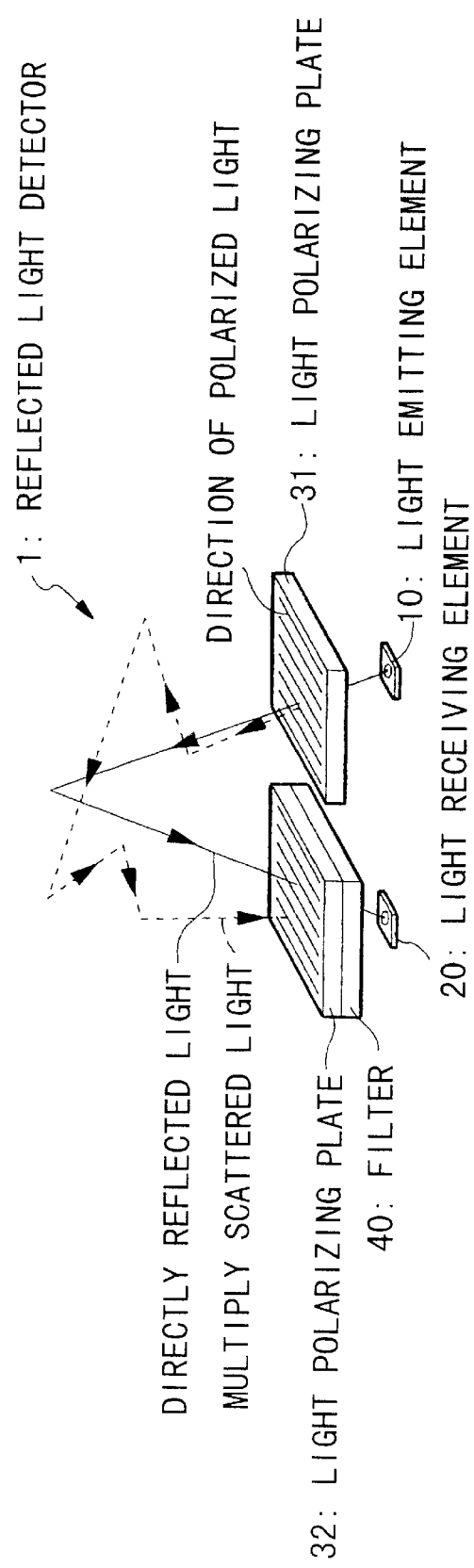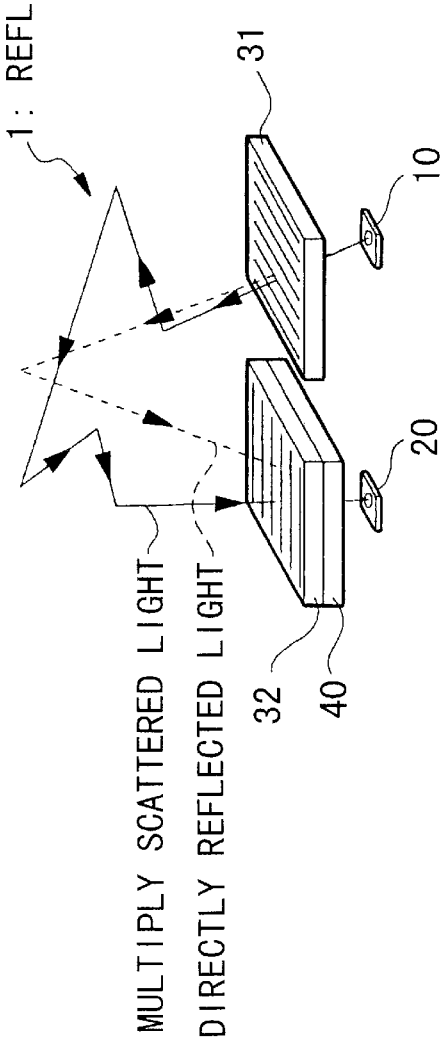

TOUCH DETECTING DEVICE, TOUCH NOTIFYING DEVICE, INFORMATION INPUTTING DEVICE, TOUCH REPLICATING DEVICE, TOUCH TRANSMISSION SYSTEM, PULSE DIAGNOSTIC DEVICE, PULSE DIAGNOSIS TRAINING DEVICE, AND PULSE DIAGNOSTIC INFORMATION TRANSMISSION DEVICE

BACKGROUND OF THE INVENTION

1. Technical Field

The present invention relates to a touch detecting device for detecting the grip state when an individual grips an object, a touch notifying device, an information inputting device that employs the touch detecting device, a touch replicating device, a touch transmission system, a pulse diagnostic device, a pulse diagnostic training device, and a pulse diagnostic information transmission system.

2. Background of the Invention

In Chinese medicine, the physician performs a pulse diagnosis by applying pressure on the skin over the patient's radius artery with his fingers. A diagnosis of the patient's physiological state is then made based on the pulse sensed by the physician through his fingers. The physician registers the pulse, referred to as sunko, in the radius artery which is located on the inner side of the wrist. The sunko pulse can be detected at three sites—upper, middle and lower, i.e., sunn, kann, and shaku sites, at the periphery. In contrast, an orally conveyed medical learning known as Ayurveda has long been known in India. As in the case of pulse diagnosis in Chinese medicine, in Ayurveda, the physician applies pressure with his second through fourth fingers on the skin over the radius artery in the patient's arm to take the pulse A technique for regularly and quantitatively performing a pulse diagnosis is disclosed in JPA No.6-197873, in which a rubber glove in which a plurality of linear distortion gauges have been affixed to sites in contact with the second through fourth finger pads is placed on the hand, and the pulse wave is detected by applying pressure on the sunko with the tips of the three fingers. In this case, the physician registers the pulse of the radius artery via the distortion gauges and the rubber glove.

In addition, Japanese Patent Application, Second Publication No. Sho57-52054 discloses a technique for detecting the pulse wave by attaching a microphone formed of a piezoelement to the three sunn, kann, and shaku sites. In this method of measurement, the pulse is directly measured without employing sensation from a person's fingers.

Normal, smooth and violent waves may be cited as representative pulse waveforms. A normal wave is characteristic of a "normal" or healthy subject, and is relaxed, having a constant rhythm without disruption. The smooth wave, on the other hand, is caused by an abnormality in the flow of blood in which the movement of the pulse becomes extremely smooth due to a mammary tumor, liver or kidney ailment, respiratory ailment, stomach or intestinal ailment, inflammation, or some other illness. On the other hand, a violent wave is caused by tension or aging of the walls of the blood vessels, and is seen in diseases such as liver and gall ailments, skin ailments, high blood pressure, and pain ailments. It is believed that the elasticity of the walls of the blood vessels decreases, so that the effect of the pulse movement of the pumped blood is not readily expressed, causing this phenomenon. The waveform of a violent wave rises violently, but does not fall off immediately, remaining at a high pressure state for a fixed period of time. In terms of the sensation registered by the fingers, a violent pulse wave feels like a straight tense and long pulse.

Pressure is applied on the radius artery during a pulse diagnosis. However, the state of the pulse registered by the fingertips will vary depending on how much pressure is applied As shown in FIG. 15, the extent of pressure P at the fingertip may be qualified as light, moderate or heavy, while the finger sensation h, which shows the strength of the pulse registered by the fingertips, may be qualified as large, medium and small. In this example, a graph in which finger sensation h is plotted on the vertical axis, and pressure P is plotted on the horizontal axis is referred to as a pressure-finger sensation trend diagram.

A typical pressure-finger sensation trend diagram is shown in FIG. 16. FIG. 16($a$) shows the pulse when finger sensation h is obtained at a moderate pressure P. A healthy individual's pulse frequently falls under this category. A pulse of this type is referred to as a "normal" pulse.

Next, when the finger sensation is obtained at a site where the pressure is relatively light, as in the case of the pressure-finger sensation trend diagram in FIG. 16($b$), then the pressure-finger sensation trend curve is referred to as a "gradually falling" curve. A gradually falling pulse is known as hua-mai. A hua-mai pulse is one in which the finger sensation h is large over pressures ranging from light to moderate. Further, if force is directed into the fingertip, then, conversely, the pulse sensation becomes weaker. A hua-mai pulse suggests the presence of an illness at the body's surface.

Next, the pressure-finger sensation trend curve in the case where a finger sensation is obtained at a site where the degree of pressure is relatively heavy, such as the pressure-finger sensation trend diagram shown in FIG. 16($c$), is referred to as a "gradually rising" curve. A gradually rising pulse is referred to as xuan-mai. In a xuan-mai pulse, the finger sensation h is large when moderate to heavy pressure P is applied. The pulse cannot be felt when only light pressure is applied by the fingertips. Rather, it is only first perceived when heavy pressure is applied. A xuan-mai pulse suggests the presence of an illness internally, that is to say, deep within the body.

It is therefore possible to know a patient's condition based on the degree of pressure applied via the fingertips in this way. In the actual pulse diagnosis, a more precise diagnosis can be performed by combining the aforementioned normal, smooth and violet pulse categories with pulse depth, i.e., hua-mai and xuan-mai pulses. However, since the physiological state of the patient is diagnosed based on subtle sensations registered by the fingers, it has been difficult to quantify and then replicate the degree of pressure applied. For this reason, it has been difficult to convey the technique of pulse diagnosis between practitioners, so that typically practice on the order of months and years is required.

Attempts have been made in the field of information machines to carry out sensing of human states or sensations. Sensing of the grip sensation when a person grips an object may be cited as one such example.

Taking the case where a person grips a cup in his hand, for example, conventional sensing of the grip sensation uses a specialized glove to measure the absolute value of the gripping force applied on the finger. This glove incorporates pressure sensors in the form of a sheet having a combination of electrodes and a pressure sensitive conductive material, the electrical resistance of which changes depending on the pressure. When the individual places the glove on his hand and grips the cup, the resistance value of the pressure sensitive conductive material changes in response to the gripping force. Thus, the absolute value of the gripping force can be known by measuring the change in the resistance value.

In the case of sensing touch sensations, such as whether or not an object is being touched by the person or what is an object's grip state (i.e., lightly gripped, strongly gripped), it is not absolutely necessary to measure the gripping force as an absolute value. Furthermore, in daily activities, a person grips an object while experiencing very subtle touch sensations. For example, in the aforementioned case of gripping a cup, the individual typically grips the cup while feeling such subtle sensations as whether the cup material is made of glass or ceramic.

However, in conventional sensing of the grip sensation, it was necessary to grip the object with a specialized glove as described above in order to achieve an objective measure of gripping force or the ability to duplicate it. For this reason, it was not possible to directly touch or grip the object, making this approach quite far off from the concept of sensing grip sensations. In addition, when a specialized glove wave adapted for use with an information inputting device like a keyboard is employed, such problems exist as the large size of the device and the burden on the operator.

Moreover, an approach might be considered in which conventional sensing of the grip sensation is applied to a pulse diagnosis, with the degree of pressure on the radius artery in the wrist being objectively detected. However, since a pulse diagnosis is carried out based on subtle sensations registered by a person's fingers, employing a specialized glove to perform the pulse diagnosis makes it impossible to detect the state of the pulse.

DISCLOSURE OF THE INVENTION

The present invention was conceived in consideration of the above-described circumstances, and has as its objective the provision of a touch detecting device capable of quantitatively detecting touch while permitting the object to be directly touched or gripped. Another objective of the present invention is the provision of an information inputting device employing the touch detecting device, a touch replicating device capable of replicating and transmitting the touch sensation, and a touch transmission system. Yet another objective of the present invention is the application of the touch detecting device in a pulse diagnosis, wherein the user applies pressure on the radius artery directly through the skin with his fingers, and the degree of this pressure is objectively detected.

In order to resolve the aforementioned problems, the invention according to claim 1 is characterized in the provision of a detecting means for receiving reflected light obtained when the detection site on the body is irradiated with light, and detecting this received light signal; and a touch information generating means for generating touch information for the detection site from the received light signal.

The invention according to claim 2 is characterized in the provision of a detecting means for receiving reflected light obtained when the detection site on the body is irradiated with light, and detecting this received light signal; a threshold value table for storing threshold values which can be used for grading the received light signal; and a touch information generating means for comparing the received light signal and the threshold value, grading the received light signal, and generating touch information in which the touch sensation at the detection site has been quantified.

The invention according to claim 3 is characterized in the provision of a detecting means for receiving reflected light obtained when the detection site on the body is irradiated with light, and detecting this received light signal; a threshold value calculating means for calculating the threshold values, which can be used for grading the received light signal, based on the light signal received when there is no pressure being applied at the detection site; a threshold value table for storing the threshold values; and a touch information generating means for comparing the received light signal and the respective threshold values, grading the received light signal, and generating touch information in which the touch sensation at the detection site has been quantified.

The invention according to claim 4 is characterized in the provision of a detecting means for receiving reflected light obtained when the detection site on the body is irradiated with light, and detecting this received light signal; a threshold value calculating means for calculating the threshold values, which can be used for grading the received light signal, based on the light signal received when there is no pressure being applied at the detection site and based on the light signal received when maximal pressure is being applied at the detection site; a threshold value table for storing the threshold values; and a touch information generating means for comparing the received light signal and the respective threshold values, grading the received light signal, and generating touch information in which the touch sensation at the detection site has been quantified.

The invention according to claim 5 is characterized in the provision of a detecting means for receiving reflected light obtained when the detection site on the body is irradiated with light, and detecting this received light signal; a calibration table for storing in advance the relationship between the received light signal and the pressure applied at the detection site; a threshold value calculating means for associating the light signal received when no pressure is applied to the detection site and the light signal received when maximal pressure is applied at the detection site, to the relationship stored in the calibration table between the received light signal and the pressure applied at the detection site, thereby calculating threshold values which can be used for grading the received light signal; a threshold value table for storing the threshold values; and a touch information generating means for comparing the received light signal and the respective threshold values, grading the received light signal, and generating touch information in which the touch sensation at the detection site has been quantified.

The invention according to claim 6 is characterized in that the threshold value calculating means calculates threshold values, which can be used for grading the received light signal, based on the DC level of the received light signal; and the touch information generating means compares the DC level of the received light signal and the respective threshold values, grades the received light signal, and generates touch information in which the touch sensation at the detection site has been quantified.

The invention according to claim 7 is characterized in that the threshold value calculating means calculates threshold values, which can be used for grading the received light signal, based on the amplitude level of the received light signal; and the touch information generating means compares the amplitude level of the received light signal and the respective threshold values, grades the received light signal, and generates touch information in which the touch sensation at the detection site has been quantified.

The invention according to claim 8 is characterized in that the threshold value calculating means calculates threshold values, which can be used for grading the received light signal, based on the ratio of the DC level and amplitude level of the received light signal; and the touch information generating means compares the threshold values with the ratio of the DC level and the amplitude level of the received light signal, grades the received light signal, and generates touch information in which the touch sensation at the detection site is quantified.

The invention according to claim 9 is characterized in that the detecting means irradiates the detection site on the body with light having a wavelength in the range of 300 to 700 nm, receives the reflected light, and detects the received light signal.

The invention according to claim 10 is characterized in that the detecting means is provided with a light generating member for generating light; a first light polarizing member for polarizing light generated by the light generating member; a second light polarizing member for incidenting reflected light from the polarized light, and permitting passage of light components polarized in a specific direction; and a light receiving member for receiving the light which has passed through the second polarizing member and outputting a received light signal in response to the amount of received light.

The invention according to claim 11 is characterized in that the detecting means is provided with a light generating member for generating light; a first light polarizing member for polarizing light generated by the light generating member; a second light polarizing member for incidenting reflected light from the polarized light, and permitting passage of light components polarized in a specific direction; and a light receiving member for incidenting the light which has passed through the second polarizing member; wherein the light receiving member comprises a light resonating member for resonating incidented light and an outputting member for outputting a received light signal in response to the light resonated by the light resonating member.

The invention according to claim 12 is characterized in that the detecting means is provided to the fingertip area.

The invention according to claim 13 is a touch notifying device provided with a touch detecting device, characterized in the provision of a notifying means for notifying the user of touch information generated by the touch information generating means.

The invention according to claim 14 is characterized in that a plurality of touch detecting means are provided, and in that the touch information is employed as input information.

The invention according to claim 15 is a touch replicating device provided with the touch detecting device, characterized in the provision of a notifying means for prompting the user so that the touch information supplied from the outside and the touch information generated by the touch information generating means approach one another.

The invention according to claim 16 is a touch replicating device provided with the touch detecting device, characterized in the provision of a comparing means for comparing the touch information supplied from the outside and the touch information generated by the touch information generating means, and a pressure means for applying pressure at the detection site based on the results of the comparison by the comparing means, so that the touch information supplied from the outside and the touch information generated by the touch information generating means coincide.

The invention according to claim 17 is a touch transmission system in which the touch detecting device is provided to the transmitting side and the touch replicating device is provided to the receiving side, characterized in the provision of a transmitting means which carries out communication between networks, and transmits touch information detected by the touch detecting device to the network; and a receiving means which carries out communication between networks, and outputs touch information supplied from the transmitting side as touch information supplied from the outside.

The invention according to claim 18 is a pulse diagnostic device provided with a pulse detecting device, characterized in the provision of a pulse diagnosing means for performing pulse diagnosis based on touch information generated by the touch information generating means.

The invention according to claim 19 is a pulse diagnostic device provided with a touch detecting device, characterized in the provision of a recording means for storing in advance standard touch information showing the degree of pressure during the pulse diagnosis; and a pulse diagnosing means for carrying out a pulse diagnosis based on the touch information generated by the touch information generating means and the standard touch information.

The invention according to claim 20 is a pulse diagnosis training device provided with touch detecting device, characterized in the provision of a recording means for storing in advance standard touch information showing the degree of pressure during the pulse diagnosis; a pulse diagnostic information generating means for generating pulse diagnostic information after grading the touch information based on the standard touch information: and a notifying means for notifying the user of the pulse diagnostic information.

The invention according to claim 21 is characterized in that the notifying means notifies the user so that the touch information generated by the touch information generating means approaches the standard touch information.

The invention according to claim 22 is characterized in that a test subject carries out pulse diagnosis by attaching the detecting means to his fingertips, and the notifying means notifies the test subjects.

The invention according to claim 23 is characterized in that a third party carries out pulse diagnosis by attaching the detecting means to the fingertips, and the notifying means notifies the third party.

The invention according to claim 24 is a pulse diagnostic information transmission system provided with a touch detecting means on the transmitting side and a touch replicating means on the receiving side, characterized in the provision of a transmitting means that carries out communications between networks and transmits touch information detected by the touch detecting device as pulse diagnostic information to the network; and a receiving means which carries out communications between networks and outputs the pulse diagnostic information from the transmitting side to the touch replicating device as touch information supplied from the outside.

The invention according to claim 25 is a pulse diagnostic information transmission system provided with a touch detecting device on the transmitting side and a touch replicating device on the receiving side, characterized in the provision of a transmitting means which generates touch information based on a received light signal obtained as a result of pulse diagnosis performed by a test subject on the transmitting side who attaches a detecting means to his fingertips, and transmits this touch information to a network as pulse diagnostic information; and a receiving means which carries out communications between networks, and outputs pulse diagnostic information from the transmitting side to the touch replicating device as touch information supplied from the outside.

The invention according to claim 26 is a pulse diagnostic information transmission system provided with a touch detecting device on the transmitting side and a touch replicating device on the receiving side, characterized in the provision of a transmitting means which generates touch information based on the received light signal obtained as a result of pulse diagnosis of a test subject on the transmitting side by a third party who attaches a detecting means to his fingertips, and transmits this touch information to a network as pulse diagnostic information; and a receiving means which carries out communications between networks, and outputs the pulse diagnostic information from the transmitting side to the touch replicating device as touch information supplied from the outside.

BRIEF DESCRIPTION OF THE FIGURES

FIG. 15 is a figure for explaining the pressure-finger sensation trend diagram.

FIG. 17(a) shows a structural overview of a pulse wave detector according to a modification of the present invention showing the structure in the case where detecting a directly reflected light component;

FIG. 17(b) is a structural overview in the case where detecting the scattered light component.

PREFERRED EMBODIMENTS OF THE PRESENT INVENTION

A. Principle of Touch Detection

Before explaining the preferred embodiments of the present invention, the principle of touch detection employed in the present invention will first be explained in terms of detection of blood flow volume and touch indicators.

1. Detection of Blood Flow Volume

When light irradiates a thin film, the ratio of the incidenting light and the transmitted light decreases by just an amount proportional to the concentration of the matter and the optical path length. This is known as the Lambert-Beer rule.

According to the Lambert-Beer rule, the matter's concentration is determined as follows.

FIG. 1 is an explanatory figure showing the Lambert-Beer rule.

Figure 1A:
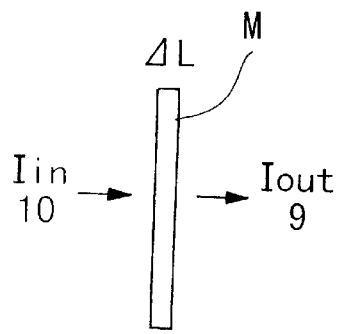
FIGS. 1A and 1B are explanatory figures showing the Lambert-Beer rule.

As shown in FIG. 1(a), the following equation may be established wherein C is the concentration of matter M, $\Delta L$ is the length of an extremely small optical path, Iin is the quantity of incidenting light, and k is the coefficient of light absorption by matter M.

$$Iout/Iin = 1 - kC\Delta L \tag{1}$$

Figure 1B:
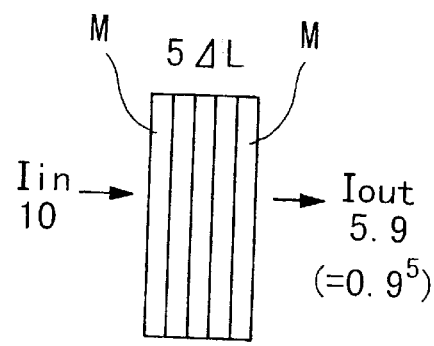

As shown in FIG. 1(b), if the optical path length is increased 5-fold, then the relationships in equation (1) changes as follows.

$$Iout/Iin = (1 - kC\Delta L)^5 \tag{2}$$

For example, if the incidenting light quantity Iin shown in FIG. 1(a) is 10, and the transmitted light quantity is 9, then for the case shown in FIG. 1(b), the transmitted light quantity is 5.9 for a incidenting light quantity of 10, i.e., Iout/Iin=$0.9^5$.

Thus, integrating equation (1), the relationship between the incidenting light volume and the transmitted light volume for an optional distance L becomes:

$$\log(Iout/Iin) = (-kCL) \tag{3}$$

Rearranging equation (3) yields:

$$Iout = Iin \times \exp(-kCL) \tag{4}$$

As may be understood from the above then, if the incidenting light quantity Iin, the absorbed light coefficient k and the optical path length L are constant, then the change in the concentration of matter M can be measured by measuring the transmitted light volume Iout.

Further, even if the light reflected by matter M is measured instead of the transmitted light volume, the change in the concentration of matter M can be measured according to exactly the same principle as described above.

When matter M is blood, then the measurement of the change in concentration is equivalent to measuring the pulsation of the blood, i.e., measuring the blood flow volume.

Figure 2:
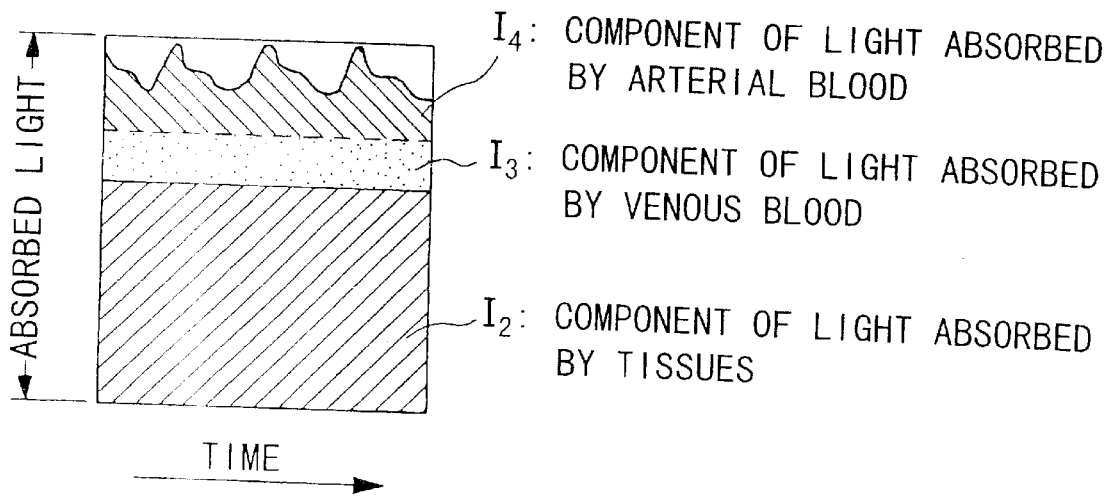
FIG. 2 is an explanatory figure showing one example of the light absorption distribution when blood vessels in a human being are irradiated with light from the outside.

FIG. 2 is an explanatory figure showing one example of the absorbed light distribution when blood vessels in a human being are irradiated with light from the outside.

In this figure, $I_2$ is the component of light absorbed by the tissues, $I_3$ is the component of light absorbed by the veins, and $I_4$ is the component of light absorbed by the arteries.

Figure 3:
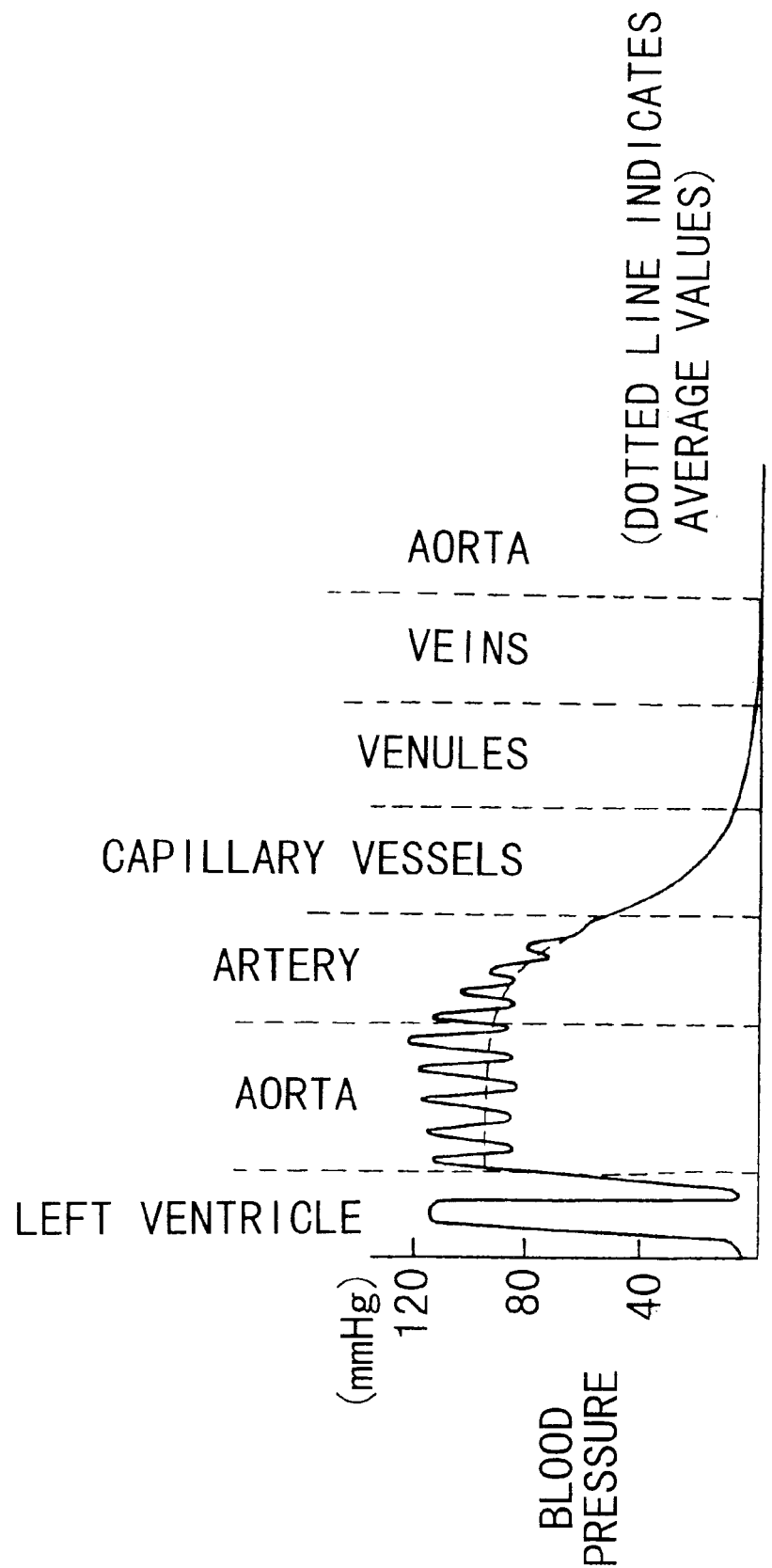
FIG. 3 is a graph showing an example of blood pressures at various sites within the body.

The component $I_2$ of light absorbed by the tissues is constant since tissue concentration does not change. The component $I_3$ of light absorbed by the veins is also constant. This is because there is no pulsation in the veins, thus, there is no change in concentration. FIG. 3 is a graph showing an example of blood pressure at sites inside the body. As may be understood from this figure, the pulsation of blood pumped out from the heart gradually dissipates as the blood moves through the body, and is completely gone by the time the blood reaches the veins. On the other hand, in the case of component $I_4$ of light absorbed by the arteries (see FIG. 2), there are concentration changes corresponding to the pulse, thus, the degree of absorbed light. Accordingly, when the blood vessels are irradiated with light, and the quantity of transmitted or reflected light is measured, these measurements include components $I_2$–$I_4$ therein. If the total of the absorbed light component $I_3$ due to venous blood and the absorbed light component $I_4$ due to arterial blood is 100%, then the proportion of absorbed light component $I_4$ due to arterial blood is 1–2% and the remaining 98–99% is absorbed light component $I_3$ due to venous blood.

2. Touch Indicators

When a person grips an object with the fingers, the pressure inside the finger rises and the blood flow volume falls. In this case, the absorbed light component $I_2$ due to tissues stays roughly constant since the tissue concentration does not change much from before or after the object is gripped. In contrast, however, both absorbed light component $I_3$ due to venous blood and absorbed light component $I_4$ due to arterial blood change since the blood volume decreases. The present invention was conceived after taking notice of this fact. By irradiating blood vessels with light, receiving the transmitted or reflected light, and then measuring the change in the light quantity, the gripping force (touch) is indirectly measured.

A venous blood component proportional to the blood flow capacity of the venous blood and an arterial blood component proportion to the blood flow capacity of the arterial blood are present in the received light quantity. For this reason, the DC component of the received light quantity is obtained by adding the average value of the arterial blood component and the venous blood component. In contrast, the AC component of the received light quantity is the amplitude of the arterial blood component. The arterial blood component is synchronized with the heartbeat, and therefore the AC component changes according to the psychological state of the test subject. For example, if the test subject is tense, then the heartbeat becomes stronger, causing the AC component to increase. Conversely, if the test subject is relaxed, then the AC component tends to decrease. In contrast, the venous blood component is not effected by the subject's psychological state, but will change depending on the environmental temperature or other such factors experienced by the test subject. Accordingly, the DC component changes from summer to winter, or afternoon to evening.

The absorbed light component $I_3$ due to venous blood is approximately 50 to 100 times greater than the absorbed light component $I_4$ due to arterial blood. Thus, the arterial blood component comprising the DC component of the received light quantity is extremely small. Accordingly, if the DC component of the received light quantity is designated as a touch indicator, then touch sensations can be measured without being subject to any psychological effect. Moreover, since the detection is performed at a large level as compared to the AC component, the S/N ratio is also good. Accordingly, in the present embodiments, the DC component of the received light quantity will be employed as the indicator for touch.

B. Embodiment 1

1. Structure of Embodiment 1

The structure of the first embodiment of the present invention will now be explained with reference to the figures.

1-1: External structure of Embodiment 1

Figure 4:
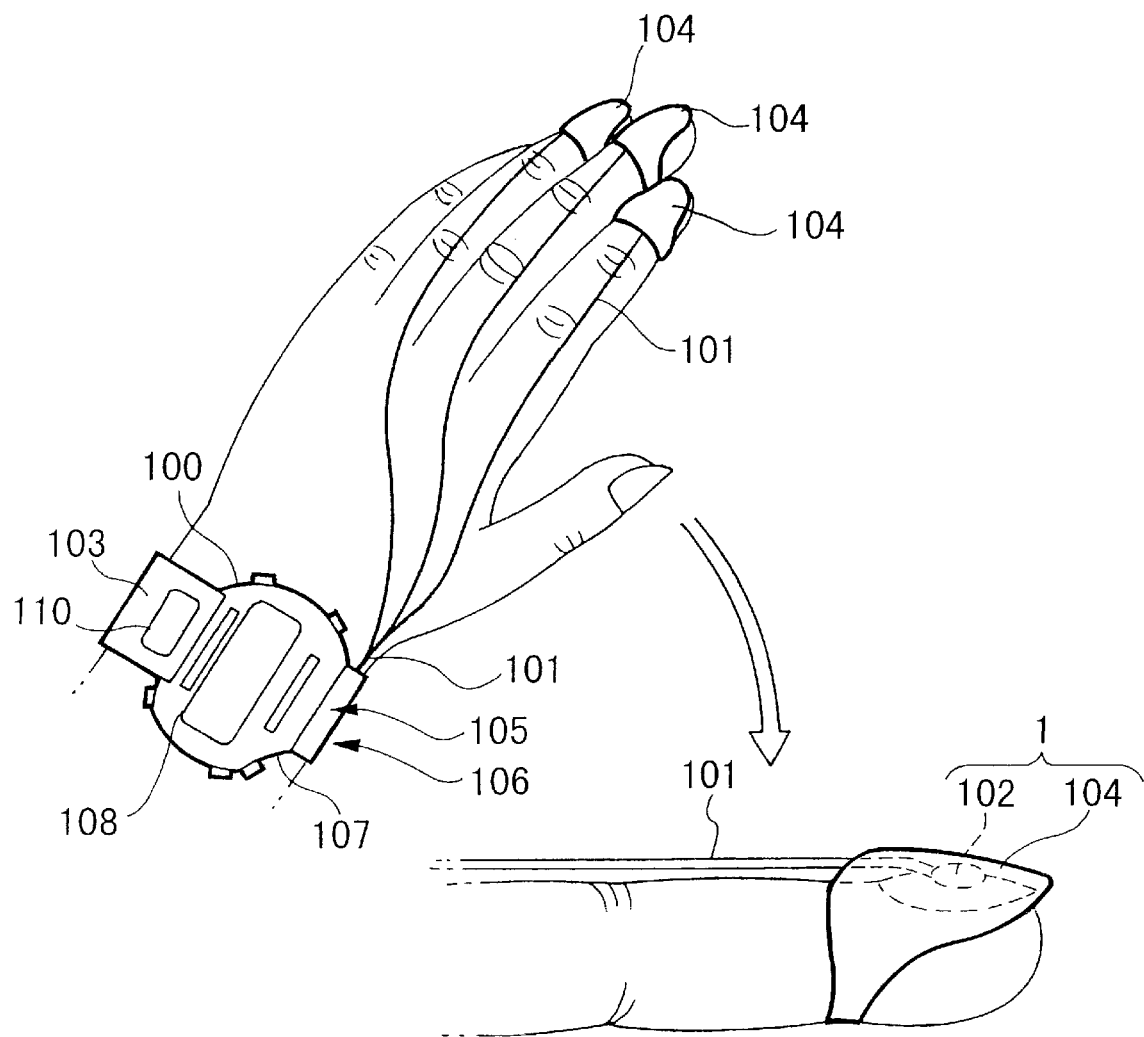
FIG. 4 is an explanatory figure showing an example of the outer structure of the touch detecting device according to a first embodiment of the present invention.

FIG. 4 is an explanatory figure showing an example of the outer structure of the touch detecting device according to a first embodiment of the present invention. As shown in FIG. 4, the touch detecting device is formed of a device main body 100 having a wristwatch structure; a cable 101 connected to device main body 100: and a pulse wave detector 1.

A wristband 103 is attached to device main body 100 which wraps around the user's wrist from the 12 o'clock position and affixes at the 6 o'clock position of the wristwatch. Device main body 100 can be freely attached and removed from the user's wrist by means of this wristband 103. A pressure sensor 110 is provided to wristband 103 on the device main body side at the 12 o'clock position on the wristwatch. Pressure sensor 110 is formed in the shape of a sheet, and is formed of a combination of electrodes and a pressure sensitive conductive material.

Pulse wave detector 1 is comprised of finger sack 104 and sensor unit 102 in which light emitting and light receiving members are formed in a unitary manner. In this example, pulse wave detectors 1 are attached to the fingertips of each of the second through fourth fingers. In this case, sensor unit 102 is provided on the inside of finger sack 104 so that it is positioned above the nail of the finger. Finger sack 104 is formed of a light-blocking material. Thus, it is possible to block external light from incidenting on sensor unit 102, so that the SN ratio for the pulse wave signal can be increased. An opening is provided in finger sack 104 on the finger pad side thereof. As a result, finger sack 104 is not a hindrance when touching or gripping an object with the pads of the fingers. Accordingly, it is possible to detect touch through natural sensations.

A connector 105 is provided at the 6 o'clock position on the face of the wristwatch. A connector piece 106, which is provided to the end of cable 101, is releasably attached to connector 105. By releasing connector piece 106 from connector 105, the device may be used as an ordinary wristwatch or stopwatch. Connector piece 105 is designed so as to be connected to a communications connector (not shown) for a personal computer. This communications connector incorporates an LED and phototransistor. In addition, an infrared interface is provided inside device main body 100 of the wristwatch, for carrying out the optical communications explained below.

Also, in order to protect connector piece 105, a specific connector cover is attached when cable 101 and sensor unit 102 are released from connector 105. With the exception of electrode components and the like, this connector cover may be formed of parts formed in the same way as connector piece 106.

As a result of a connector design as formed above, connector 105 is disposed toward the user, facilitating its manipulation. In addition, since connector 105 does not extend out from device main body 100 in the 3 o'clock position, the user can freely move his wrist during exercise. Thus, even if the user falls during exercise, the back of the hand will not impact connector 105.

Device main body 100 is provided with a watch case 107 made of a resin. A liquid crystal display 108 is provided to the face of watch case 107 which displays in digital form the current time and date, as well as touch information SJ such the gripping force. LCD device 108 is comprised of first, second, and third segment display regions (not shown) and a dot display region. The first segment display region displays the date, day of the week and current time. The second segment display region displays the passage of time when carrying out various time measurements. The third segment display region displays various measured values obtained when measuring touch. The dot display region graphically displays various information, in addition to a variety of other displays such as a mode display, which indicates which mode the device is in at a particular time, pulse waveform display, bar graph display and the like.

Note that the term "mode" as used here refers to a variety of modes such as a mode for setting the time and date, a mode for using the device as a stop watch, a touch mode for using the device as a touch detecting device, and the like.

1-2: Electrical structure of Embodiment 1

Figure 5:
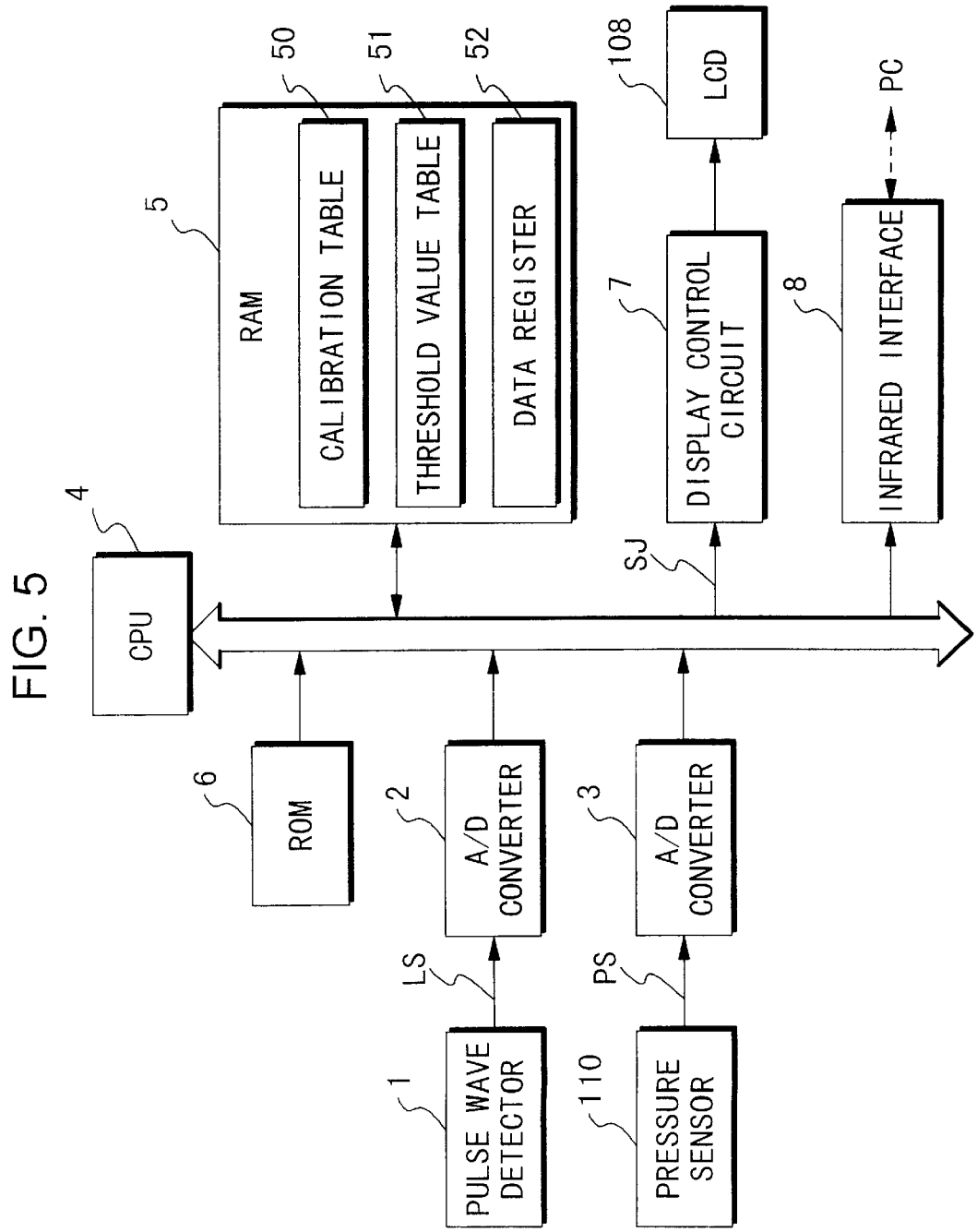
FIG. 5 is a block diagram of the touch detecting device according to this same embodiment.

Next, the electrical structure of the touch detecting device will be explained with reference to FIG. 5. FIG. 5 is a block diagram of the touch detecting device according to a first embodiment of the present invention.

In FIG. 5, numbers 2 and 3 indicate A/D converters which respectively convert the received light signal LS from pulse wave detector 1 and the pressure signal PS from pressure sensor 110 to digital data. Note that it is sufficient that the DC component of the received light level, the touch indicator, be a relative value. Thus, it is not necessary that pressure sensor 103 be a precise device for detecting absolute values, rather a presser sensor 103 that detects relative values is sufficient.

Numeral 4 indicates a CPU (central processing unit) which controls all parts of the main device via a bus. 5 is a RAM (random access memory), comprising a calibration table 50 employed when detecting touch, a threshold value table 51 employed when grading touch information SJ, and data register 52 for storing various data. 6 is a ROM (read only memory) in which the control programs employed in CPU 4 are stored. 7 is a display control circuit which displays touch information SJ and time information on LCD 108, based on the display data sent by CPU 4. 8 is an infrared interface for carrying out communications with personal computer PC.

Figure 6:
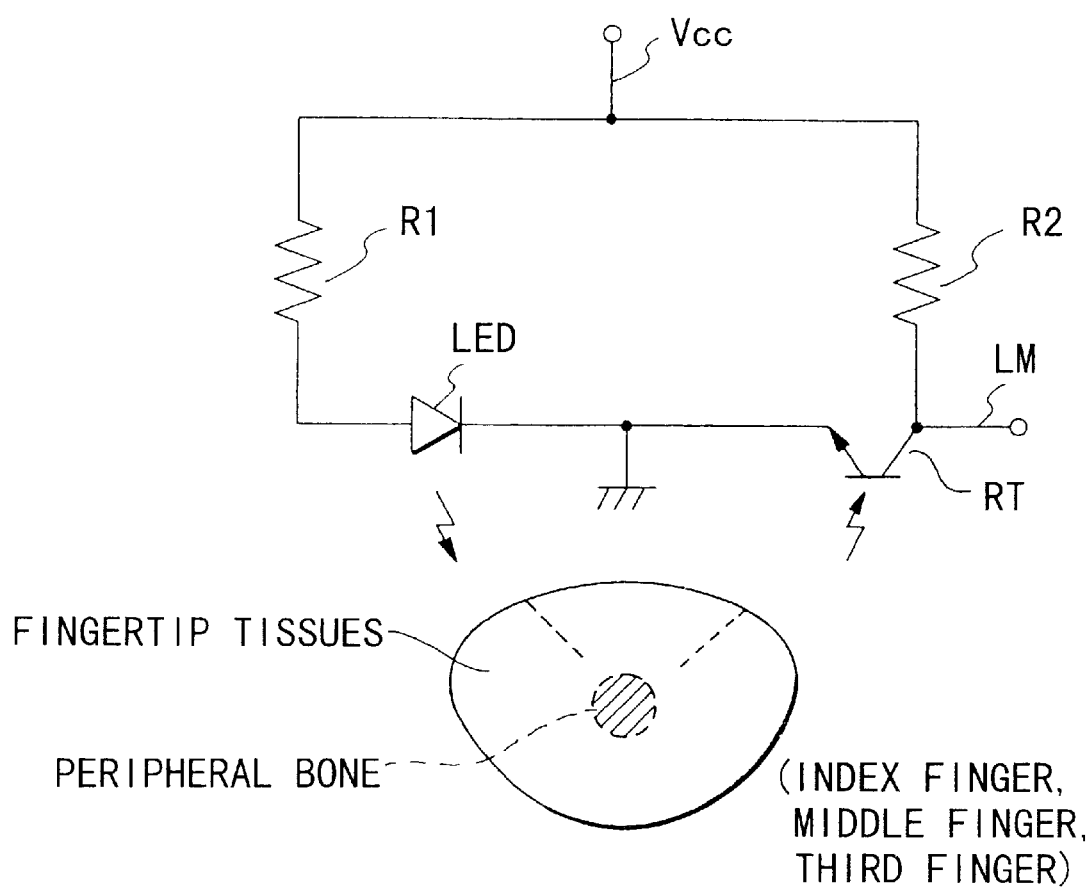
FIG. 6 is a circuit diagram showing the detailed structure of pulse wave detector 1 employed in the same embodiment.

The detailed structure of pulse wave detector 1 will now be explained using the circuit diagram shown in FIG. 6. In FIG. 6, resistor R1 and LED correspond to the light emitting member, while resistor R2 and photo transistor PT correspond to the light receiving member. When a voltage Vcc from the power source is impressed on pulse wave detector 1, light is irradiated from the LED. After being reflected by the blood vessels and tissues, the light is received at photo transistor PT. If the quantity of received light is increased, the base current of photo transistor PT increases, and the collector voltage (the level of received light signal LS, hereinafter referred to as "received light level") decreases. The wavelength of the light emitted from the LED is selected to be near the absorption wavelength peak for blood hemoglobin. Thus, the received light level changes in response to the blood flow volume, and the blood flow volume changes in response to the pressure applied on the finger. Accordingly, by detecting the received light level, it is possible to detect the touch sensation registered by an individual when gripping an object.

An InGaN-type (indium-gallium-nitrogen) blue LED is suitably employed for the LED. The generated light spectrum of a blue LED has a peak at 450 nm, for example, with the generated light wavelength region being in the range of 350 to 600 nm. In this case, a GaAsP-type (gallium-arsenic-phosphorous) photo transistor PT may be used for the photo transistor PT corresponding to the LED having the light emitting characteristics described above. The received light wavelength region of photo transistor PT has, for example, a main sensitive region in the range of 300 to 600 nm, with a sensitive region also present below 300 nm.

When a blue LED and photo transistor PT such as described above are combined, the pulse wave is detected in the overlapping wavelength region of 300 to 600 nm. This offers the following advantages.

In the case of outside light, it tends to be difficult for light having a wavelength region of 700 nm or less to pass through the tissues of the finger. For this reason, even if the portion of the finger not covered by finger sack 104 is irradiated with outside light, the light does not reach photo transistor PT through the finger tissue. Rather, only light in the wavelength region which does not influence the detection reaches photo transistor PT. On the other hand, light in the low wavelength region from 300 nm is almost entirely absorbed at the skin surface. Thus, even if the received light wavelength region is set to 700 nm or less, the actual received light wavelength region is 300 to 700 nm. Accordingly, it is possible to control the impact of outside light, without having to significantly cover the finger.

Moreover, the absorption coefficient of blood hemoglobin with respect to light having a wavelength of 300 to 700 nm is large, and is several to 100-fold greater than the absorption coefficient with respect to light having a wavelength of 880 nm. Accordingly, as in this example, when light in the wavelength region (300 to 700 nm) having large absorption characteristics matching the absorption characteristics of hemoglobin is employed as the light which is detected, the detected values therefor vary with good sensitively in response to changes in blood volume. Thus, it is possible to increase the S/N ratio of the pulse wave signal which is based on the change in blood volume.

Figure 7:
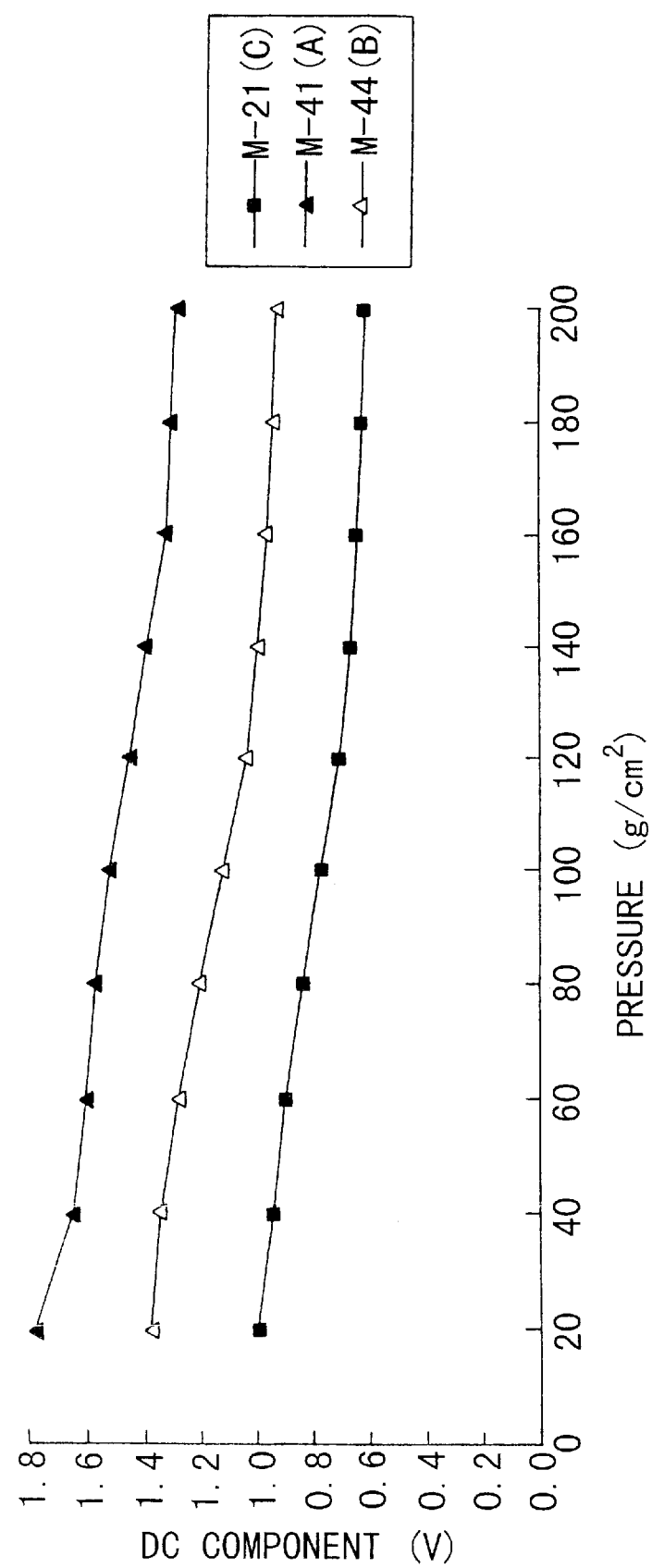
FIG. 7 is a graph showing the relationship between the received light level and the pressure measured for three test subjects.

In the case where a person is applying pressure with his fingers, individual differences emerge with respect to the relationship between the pressing force and the received light level. This point will be explained with reference to the figures. FIG. 7 is a graph showing the relationship between pressing force and the DC component of the received light level. The black triangle, white triangle, and black square represent the results obtained for measurements on a 21 year old male (test subject A), 41 year old male (test subject B), and 44 year old male (test subject C), respectively. So that it is not effected by the changes in blood flow volume in synchronization with arterial blood, the DC component of the received light level is measured using a low pass filter having a sufficiently low cut-off frequency.

As shown in FIG. 7, when the pressing value is varied from 20 g/cm$^2$ to 200 g/cm$^2$, the DC component associated with test subject A changes from 1.8 V to 1.4 V, the DC component associated with test subject B changes from 1.4 V to 0.95 V, and the DC component associated with test subject C changes from 1.0 V to 0.65 V. Thus, while the DC component of the received light level tends to decrease monotonously when the pressing value is increased, it may be understood that the range of this variation differs depending on the test subject. In other words, individual differences may be seen in the relationship between pressing force and the received light level. This is due to the fact that there are differences between individuals with respect to the thickness of the blood vessels, the amount of hemoglobin in the blood, and the tissue elasticity coefficient, for example.

The reason that the DC component of the received light level decreases monotonously when the pressing value is increased is as follows. Namely, when the finger is pressed down, the pressure inside the finger rises, while the blood flow volume falls. This is accompanied by a reduction in the absorption by hemoglobin. For this reason, the quantity of reflected light which has incidented on the light receiving member increases and the received light level falls.

The AC component of the received light level varies according to the psychological state of the test subject, while the DC component changes according to the environmental temperature and other such conditions experienced by the test subject. Accordingly, even in the same individual, differences will exist in the relationship between pressing force and the received light level.

This embodiment grades the touch sensation registered by the finger based on the DC component of the received light level. However, as explained above, the relationship between the pressing force and the received light level will differ between individuals as well as within the same individual. Thus, the touch information SJ obtained here is relative data.

When grading the touch sensation, some sort of threshold value is required. Since the relationship between the pressing force and the received light level will differ between individuals and within the same individual, it is necessary to correct the received light level when measuring touch information SJ. Pressure sensor 110 is provided for this purpose.

2: Operation of Embodiment 1

Next, the operation of the first embodiment will be explained with reference to the figures.

(1) Generation of Calibration Table

Prior to measuring touch information SJ, a calibration table 50 is generated in the touch detecting device. When device main body 100 is operated to place it in the touch detecting mode, CPU 4 displays the message "attach finger band, press button when ready" on LCD 108. Prompted by the message, the user attaches pulse wave detectors 1 to the fingertips of each of the fingers, and presses the button. Once CPU 4 has detected manipulation of the button, it displays the message "remove wristwatch, press button when ready" on LCD 108.

Following the prompt, the user removes device main body 100 from his arm and presses the button. When CPU 4 detects this, it performs digital filter calculations to obtain the DC component from the received light level. The DC component of the received light level is stored in data register 52. Since pressure is not being applied to the finger in this case, the DC component of the received light level that is stored shows the maximum value Lmax of the received light level. Thereafter, CPU 4 displays the message "slowly press finger against pad" on LCD 108. Prompted by the message, the user presses down on pressure sensor 110 by gradually applying force into the finger. CPU 4 stores the relationship between the DC component of the received light level and the degree of pressure which are changing over time in calibration table 50.

(2) Generation of Threshold Value Table

After the passage of a specific period of time, CPU 4 displays the message "Please apply more force" on LCD 108. As a result, the user presses pressure sensor 110 with maximal force. Pmax, the maximum value for the degree of pressure, and Lmin, the minimum value for the DC component, are detected at this time, with these values stored in data register 52.

Next, CPU 4 reads out the maximum value Pmax for the degree of pressure from data register 52, equally divides maximum value Pmax in response to the number of gradings, and determines each of the threshold values for the degree of pressure. For example, assuming a maximum value Pmax=200 $g/cm^2$ and 5 step grading, then the threshold values for each of the degree of pressures are 0, 40, 80, and 160 $g/cm^2$.

Next, CPU 4 refers to calibration table 50, and determines each of the received light levels in response to each of the threshold values for the degree of pressures. These values are stored in threshold value table 52 as threshold values for the received light levels. In other words, the received light levels when pressure is not being applied and when pressure is being maximally applied are correlated with the relationship between pressing force and the received light level stored in calibration table 51, and the threshold values, which are the standard when grading the received light level, are determined.

Note that the generation of calibration table 50 and threshold value table 52 is performed for each finger of the hand.

(3) Measurement of Touch Information

Once generation of threshold value table 51 is completed, CPU 4 displays the message "fasten device to arm with band, push button when ready" on LCD 108. Prompted by the message, the user wraps wristband 103 around his arm to fix device main body 100 in place, and presses the button. CPU 4 detects depression of the button, and displays the message "touch-sensing mode" on LCD 108. When the person grips an object thereafter, the person feels the reaction force from the object in the fingers as the touch sensation. When the received light signal LS detected by pulse wave detectors 1 is input to device main body 100, the CPU compares the received light level at each specific sample timing with each of the threshold values stored in threshold value table 51, grades the received light level, and generates these results as touch information SJ. This touch information SJ is stored in data register 52, and sent to LCD 108 for display there.

C. Embodiment 2

The second embodiment of the present invention relates to a touch transmission system employing the touch detecting device explained in the first embodiment, this touch transmission system transmitting touch such as grip sensation from the site at which measurements were made to another point some distance away.

1. Structure of the Touch Transmission System

Figure 8:
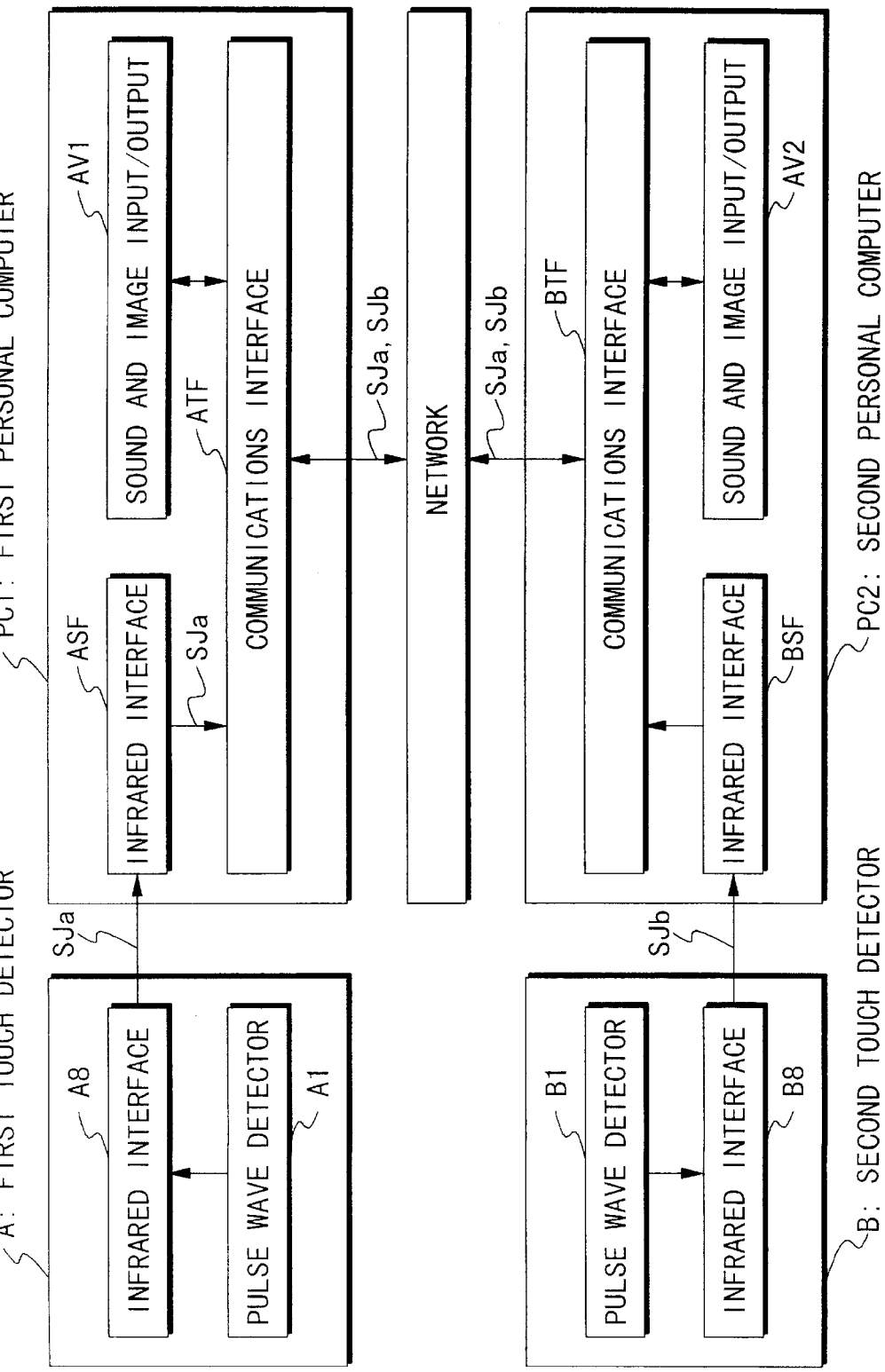
FIG. 8 is a block diagram of the touch transmission system according to a second embodiment of the present invention.

The structure of the touch transmission system according to the second embodiment will now be explained with reference to the figures. FIG. 8 is a block diagram of a touch transmission system. In the figure, first and second personal computers PC1 and PC2 are provided with sound and image input and output members AV1 and AV2. Sound and image input and output members AV1, AV2 are comprised of a microphone for the sound input member, a camera for the image input member, a speaker for the sound output member, and a display for the image output member (not shown in the figures). First and second personal computers PC1,PC2 are each provided with infrared interfaces ASF, BSF for communicating with the first and second touch detecting devices A,B via infrared rays. Communication interfaces ATF,BTF function as transmitting and receiving means for first and second touch information SJa,SJb, and carry out communications between first and second personal computers PC1,PC2 via a network NET.

2. Operation of the Touch Transmission System

Next, the operation of the touch transmission system according to a second embodiment of the present invention will now be explained with reference to the figures. In this example, the system is applied to a golf lesson, with the instructor on the first touch detecting device A, and the student on the second touch detecting device B.

The instructor and student each attach pulse wave detectors 1 to each of the fingers on both hands. When the instructor grips the golf club, touch information SJa corresponding to the gripping force of each finger is detected by first touch detecting device A. When this touch information SJa is relayed to first personal computer PC1 via infrared interface A8, first personal computer PC1 sends the touch information SJa to second personal computer PC2 via network NET. Conversely, when the student grips the golf club, the touch information SJb detected at this time is sent to first personal computer PC1 via the opposite pathway.

Figure 9:
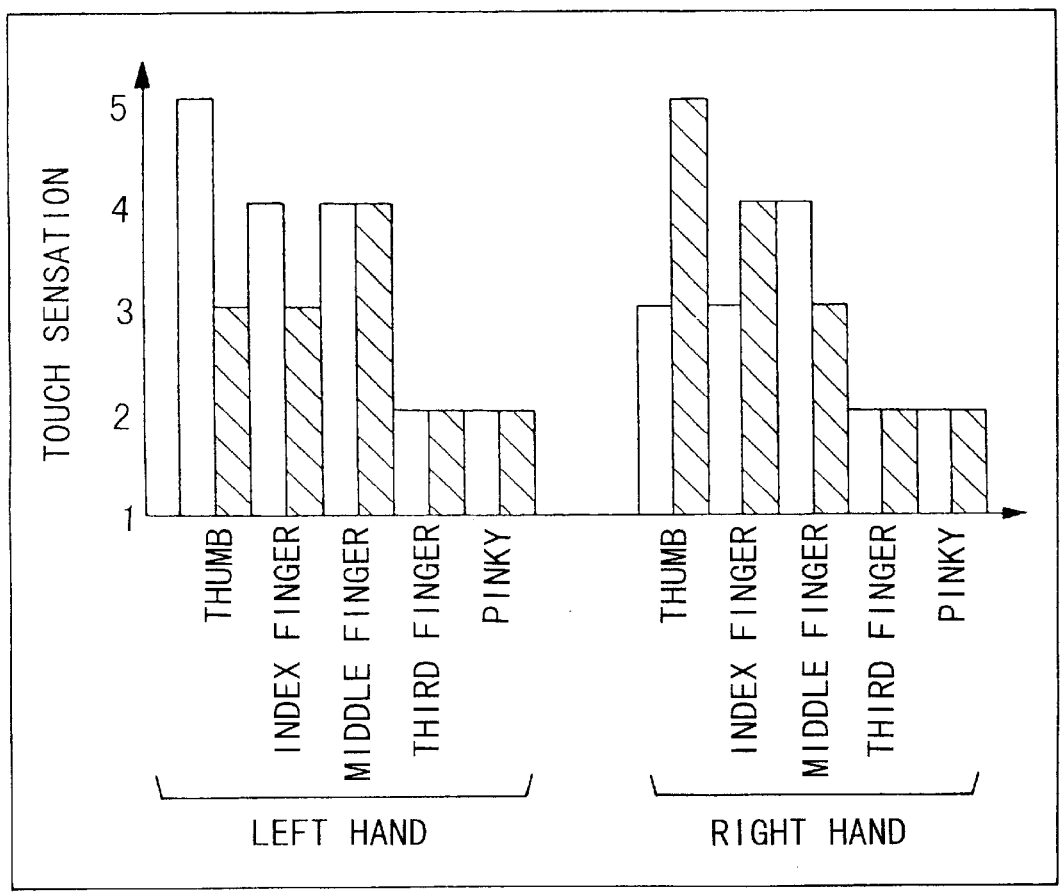
FIG. 9 is an explanatory figure for explaining one example of a screen shown on the display of the first and second personal computer according to the same embodiment.

The screen shown in FIG. 9 is displayed on the display which forms sound and image input and output members AV1,AV2, for example. The white bar on the screen is generated based on touch information SJa from the instructor, while the hatched bars are generated based on touch information SJb from the student. When the instructor determines that the student is directing too much force into his right hand based on this screen, then the instructor can advise the student "to apply more force to the thumb and index finger of the left hand and touch the club lightly with the right hand". Using the screen and the advice received from the instructor, the student can then increase or decrease the force applied to each of the fingers so that the hatched bars match the white bars on the screen.

In this example, touch information SJa and SJb are information in which the relative touch has been quantified. Thus, while it is not possible to make the absolute values of the gripping force equivalent, the instructor is able to convey his sensation of gripping the golf club to the student.

D. Embodiment 3

The touch detecting device explained in the first embodiment enables grading the degree of pressure as touch information, without impairing the user's sensation of touching an object with his fingers. Thus, if the above-described touch detecting device is applied in a pulse diagnosis, the degree of pressure can be graded, enabling the degree of pressure applied by a physician skilled in pulse diagnosis to be conveyed objectively to a third person. The third embodiment of the present invention relates to a pulse diagnostic device that employs the touch detecting device.

1. Structure of Embodiment 3

Figure 10:
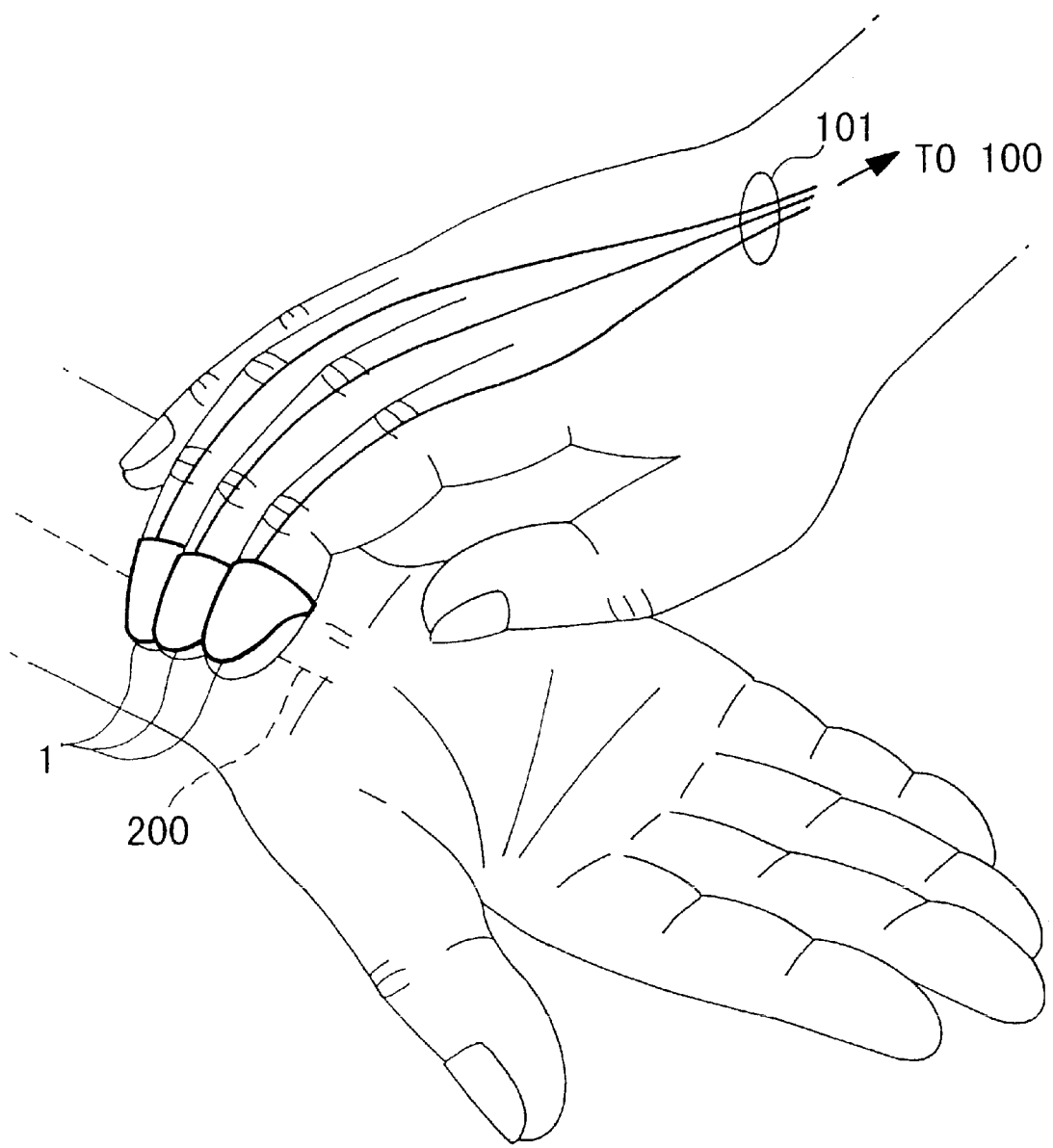
FIG. 10 is an explanatory figure showing the state of use of the pulse diagnostic device according to the third embodiment of the present invention.

The external structure of the pulse diagnostic device according to a third embodiment of the present invention is similar to that of the touch detecting device in the first embodiment shown in FIG. 4. FIG. 10 is an explanatory figure showing the usage state of the pulse diagnostic device. In this example, the user attaches pulse wave detector 1 to the tips of the fingers on the right hand, and presses down on the patient's radius artery 20 via the overlying skin. In this case, pulse wave detectors 1 are attached to the index, middle and third fingers.

As a result, the user registers the so-called sunkou pulse from the radius artery located on the inside of the wrist. The sunkou pulse is detected at three sites—upper, middle and lower, i.e., sunn, kann, and shaku sites. Here, sunn indicates the wrist pulse at the periphery, with the sunn pulse expressing the individual's state of health from head to the chest. The sunn pulse is detected by the index finger. Kann indicates the pulse at an intermediate location between the periphery and the heart, with the kann pulse expressing the individual's state of health from chest to heart. The kann pulse is detected by the middle finger. Shaku indicates the pulse at the heart, with the shaku pulse expressing the individual's state of health from heart to legs. The shaku pulse is detected by the third finger.

Figure 11:
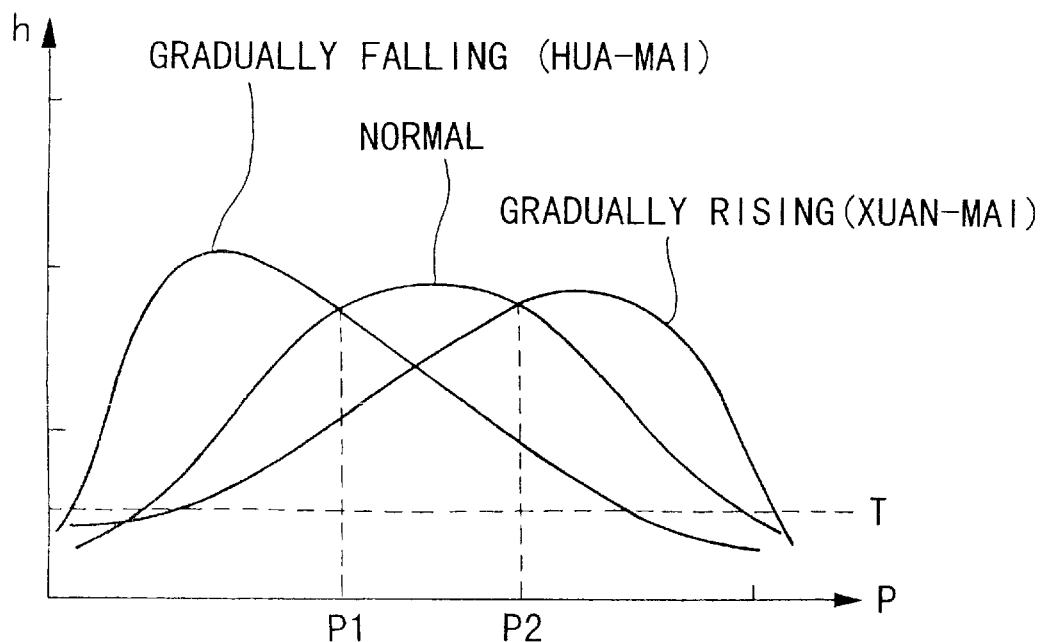
FIG. 11 is an explanatory figure showing the relationship between the threshold values and the pressure-finger sensation trend curve according the same embodiment.
Figure 16A:
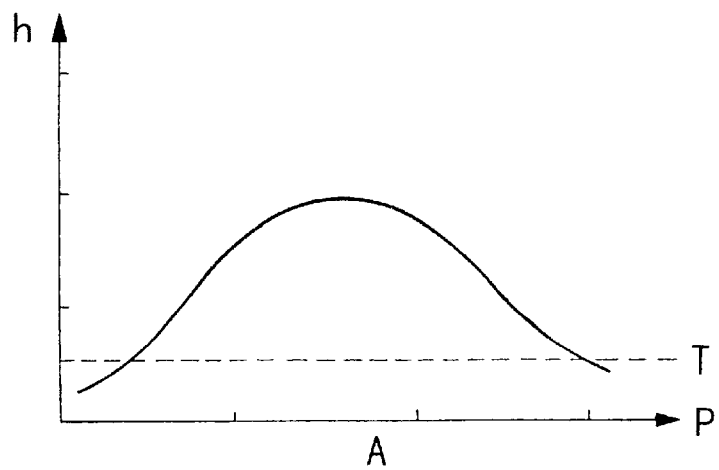
FIGS. 16A, 16B and 16C show a representative pressure-finger sensation trend curve.
Figure 16B:
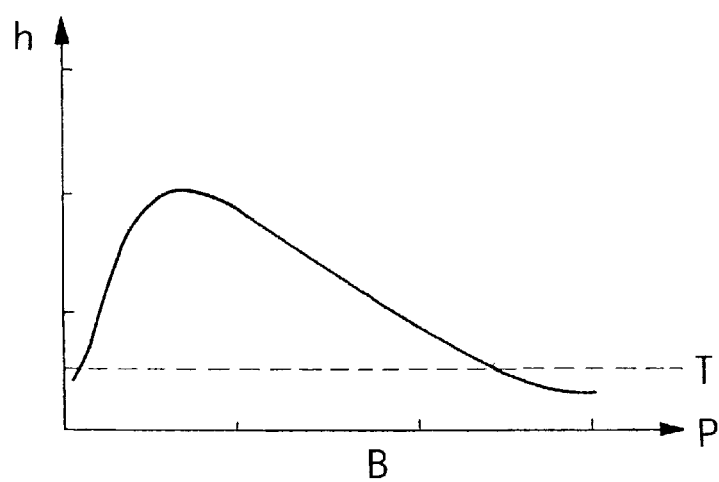
Figure 16C:
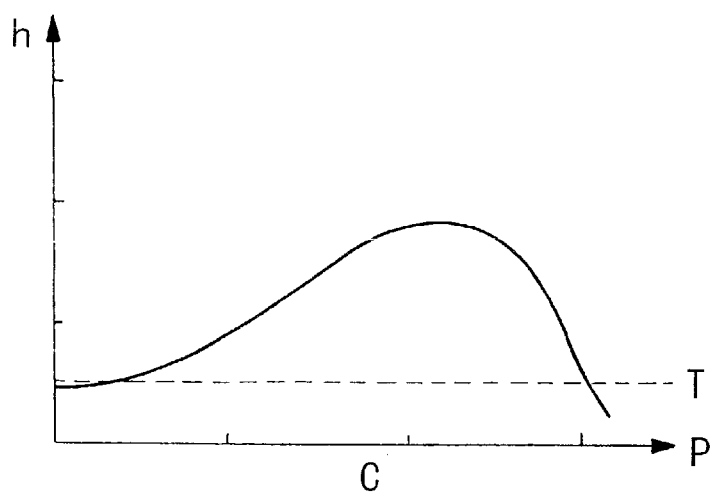

The electrical structure of the pulse diagnostic device is similar to the structure of the touch detecting device in Embodiment 1 shown in FIG. 4. However, the relationship between finger sensation h and touch information (pressure P) when a skilled physician conducts a pulse diagnosis is stored in ROM 6 as a table for each of the pressure-finger sensation trend curve types, i.e., normal, gradually falling and gradually rising (see FIG. 16). In addition, threshold values P1,P2 shown in FIG. 11 are also stored in ROM 6 so that the type of pressure-finger sensation trend curve can be determined. From this perspective, ROM 6 functions as a storing means for storing in advance standard touch information showing the degree of pressure when performing a pulse diagnosis.

2. Operation of Embodiment 3

The operation of the pulse diagnostic device according to a third embodiment of the present invention will now be explained with reference to the figures. Note that the generation of (1) the calibration table and (2) the threshold value table explained in the operation of the first embodiment is assumed as a precondition to performing the pulse diagnosis.

First, the user operates device main body 100 to select the pulse diagnostic mode. The user then attaches pulse wave detectors 1 to his fingertips as shown in FIG. 10. Next, the user presses down on the patient's radius artery 200 with his index, middle and third fingers. As a result, pulse wave detectors 1 attached to each of the fingertips detect received light signals LS, and output these signals to device main body 100. CPU 4 compares the received light level at each specific sampling with the threshold values stored in threshold value table 51, grades the received light level, and generates these results as touch information SJ. Touch information SJ is the reactive force applied on the fingers from the skin tissues and blood vessels during pressing. Thus, it indicates the pressure P shown in FIG. 16 and FIG. 11.

Figure 12:
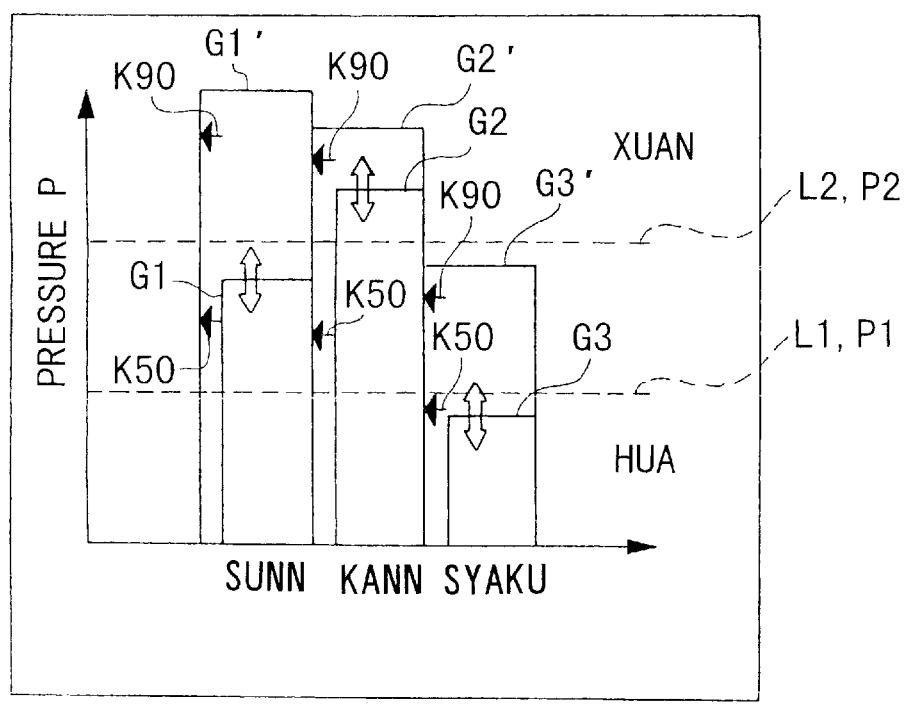
FIG. 12 shows an example of the display appearance on the liquid crystal display member according to the same embodiment.

Under the control of CPU 4, touch information SJ is sent to LCD 108 and displayed there. FIG. 12 shows an example of the display state on LCD 108. In this case, bar graph G1, corresponding to the sunn value, is displayed based on touch information SJ obtained from the index finger, bar graph G2, corresponding to the kann value, is displayed based on touch information SJ obtained from the middle finger;.and bar graph G3, corresponding to the shaku value, is displayed based on touch information SJ obtained from the third finger. Bar graphs G1~G3 rise or fall according to changes in the degree of pressure by each finger. Accordingly, the user can visually confirm the degree of pressure by each finger. In addition, using the displays on bar graphs G1~G3, in which the length and display of partitioning lines L1,L2 change, the user is able to know the degree of pressure corresponding to a xuan-mai pulse, for example. Specifically, if the pressing state is that shown in FIG. 12, then by slightly increasing pressing by the index finger, the user is able to know the degree of pressure corresponds to a xuan-mai pulse. In this case, LCD 108 functions as a notifying means for notifying the user so that pressing (touch information SJ) approaches threshold values P1,P2 (standard touch information).

Partitioning line L1 shown at the upper part of FIG. 12 corresponds to threshold value P2 read out from ROM 6, while partitioning line L2 shown at the bottom part of FIG. 12 corresponds to threshold value P1. When a maximum finger sensation h is obtained when the bar graph exceeds partitioning line L1 (i.e., when the pulse is felt clearly), then the pressure-finger sensation trend curve is a gradually rising curve, and the pulse is determined to be a xuan-mai pulse. When a maximum finger sensation h is obtained when the bar graph falls below partitioning line L1, then the pressure-finger sensation trend curve is a gradually falling curve, and the pulse is determined to be a hua-mai pulse.

When a button on pulse diagnostic device main body 100 is operated, then the bar graphs G1~G3 displayed on LCD 108 can be maintained at their peak values. Bar graphs G1'~G3' are the result obtained when the peak levels in bar graphs G1~G3 are maintained. Here, bar graph G1' is displayed based on the maximum value of touch information SJ obtained from the index finger; bar graph G2' is displayed based on the maximum value of touch information SJ obtained from the middle finger; and bar graph G3' is displayed based on the maximum value of touch information SJ obtained from the third finger. Note that the maximum value is obtained as a result of CPU maintaining touch information SJ at peak levels. Accordingly, by pressing while watching LCD 108, the user is able to know the finger sensation at maximal pressing. Arrows K90 displayed inside bar graphs G1'~G3' indicate 90% of the maximal level on each of the graphs. Arrows K50 indicate 50% of the maximal level on each of the graphs. As a result, it is possible for the user to confirm what the finger sensation is when pressing at 50% or 90% of the maximum level.

In this example, the user can confirm whether bar graph 2 is rising or falling while sensing the degree of pressure by the fingertips. Thus, the user can adjust the degree of pressure by each of the fingers, so that he understands the degree of pressure, i.e., the hua or xuan, registered by a skilled physician. Moreover, for example, when the sunn pulse is detected to be a hua-mai pulse, a determination can be made that a mammary tumor or the like may have occurred in the area from the head to the chest. When the kann pulse is detected to be a xuan-mai smooth pulse, a determination may be made that a gastrointestinal disease may be present.

In a pulse diagnosis, the examiner repeatedly increases and decreases the pressing force while searching for the degree of pressure at which the pulse can be felt most clearly. The finger sensation h changes in response to the degree of pressure P, and categorizing the pressure-finger sensation trend curve according to this arrangement is as described above. Accordingly, if not only the degree of pressure at which the pulse can be most clearly registered, but also the state of the pulses which precede and proceed this point can be known, then a user who is not familiar with pulse diagnosis is able to more objectively understand the pulse state, i.e., whether the pulse is a hua-mai pulse or a xuan-mai pulse.

Figure 13:
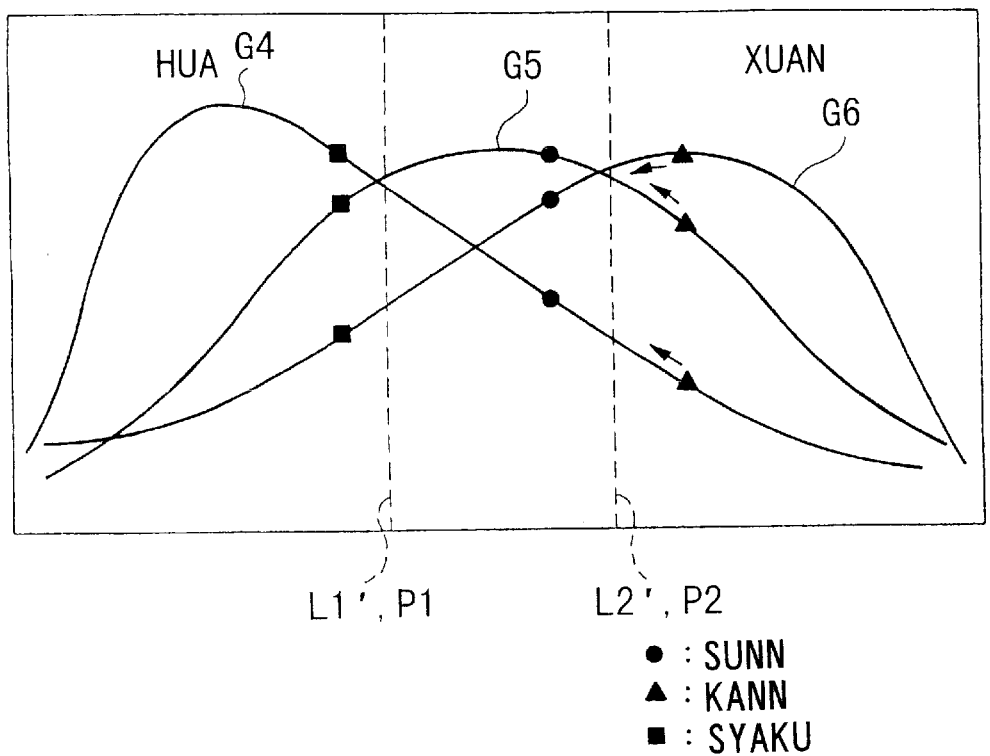
FIG. 13 shows another example of the display appearance on the liquid crystal display member according to the same embodiment.

The screen shown in FIG. 13 may be displayed on LCD 108. Pressure-finger sensation trend curves G4~G6 shown in FIG. 13 are read-out from each of the tables stored in ROM 6 and displayed. In this example, gradually falling curved line G4 is displayed in blue, normal curved line G5 is displayed in green, and gradually rising curved line G6 is displayed in red. Partitioning line L1' on the left side corresponds to threshold value P1, while partitioning line L2' on the right side corresponds to threshold value P2. Next, the black circles are indicator points corresponding to sunn pressures, and are displayed based on touch information SJ obtained from the index finger. The black triangles are indicator points corresponding to kann pressures, and are displayed based on touch information SJ obtained from the middle finger. The black squares are indicator points corresponding to shaku pressures, and are displayed based on touch information SJ obtained from the third finger. Each of these indicator points changes in response to changes in the degree of pressure at each finger, moving along pressure-finger sensation trend curves G4~G6.

Take, for example, the kann pressure. If the user reduces the degree of pressure from the state showing in the figure, then the black triangle indicator points move in the direction of the arrow. At this time, if the user feels that the pulse state is gradually becoming less clear, he may determine that this pulse is a xuan-mai pulse. Conversely, if the user feels that the pulse is gradually becoming clearer, the indicator points are shifting to the left side of partitioning line L1' and the clarity is increasing, then he can make a determination that this pulse is a hua-mai pulse.

In this example, indicator points moved along a representative pressure-finger sensation trend curve in response to the degree of pressure P. As a result, the user registers the clarity of the pulse via his fingertips while watching the movement of the indicator points. Thus, he is able to classify the pulse type. Accordingly, it is possible to increase the accuracy of the pulse diagnosis.

E. Effects of the Embodiments

As explained above, the present embodiments enables detection of touch information in which the touch sensation has been quantified, in a state such that the user is able to directly touch or grip an object. In addition, because the structure of the device is simple, there is no burden on the test subject. Detection of subtle touch sensations, such as whether or not an object is being touched, is also possible. Transmission and duplication of relative touch can also be performed. It is also possible for the user to understand objectively the pulse diagnosis degree of pressure. More specifically, the following effects corresponding to each of the embodiments are offered.

In the first embodiment, pulse wave detector 1 is formed of a sensor unit 102 and finger sack 104 so that it can be attached to the fingertips of each of the fingers. Thus, the user can directly touch or grip an object. As a result, there is no need for the user to don a specialized glove, thus the burden on the operator is reduced and detection of touch can be performed as a pure sensation. In addition, in the first embodiment, a calibration table 50 was prepared in advance, and the light level received when no pressure is applied at the detection site and the light level received when maximal pressure is applied at the detection site is associated with the relationship between the received light levels stored in calibration table 50 and the pressing force. The threshold values are determined, and the grading of the received light level is performed based on these threshold values. Thus, it is possible to quantify the touch sensation registered when the person touches or grips an object.

In the second embodiment, first and second personal computers PC1 and PC2 are connected via a network NET.

Thus, touch information SJa,b detected by first and second touch detecting devices A,B are alternately transmitted.

In the third embodiment, the touch detecting device is applied to a pulse diagnostic device. As a result, it is possible for the user to understand the degree of subtle pressure which is required in a pulse diagnosis. For this reason, it is possible for the user to physically experience the degree of pressure, which previously could only be understood in terms of words such as "light" or "heavy". Thus, a determination of pulse phenomenon, i.e., hua-mai or xuan-mai pulses, can be made easily.

F. Modifications

The present invention is not limited to the preceding embodiments. Rather, a variety of modifications as follows are also possible.

Figure 14A:
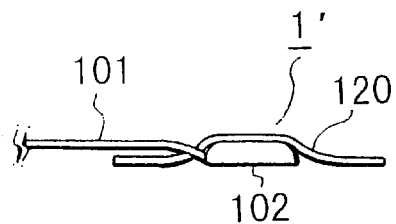
FIG. 14(A) is a cross-sectional diagram showing an example of the structure of pulse wave detector 1' according to a modification of the present invention.
Figure 14B:
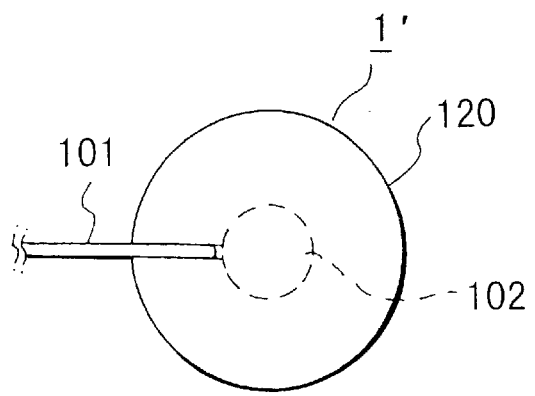
FIG. 14(B) is a planar view thereof.

(1) In each of the preceding embodiments, pulse wave detector 1 was described as attaching to each of the fingers of the hand. However, the design shown in FIG. 14 is also acceptable. FIG. 14(A) is a cross-sectional view of pulse wave detector 1' according to a modification, while FIG. 14(B) is a planar view thereof. Pulse wave detector 1' is formed of a sensor unit 102 to which a cable 101 is attached, and adhesive pads 120. An adhesive material is coated to the bottom of adhesive pad 120, so that pulse wave detector 1' can detect blood flow by being affixed to the detection site on the body. If pulse wave detector 1' is affixed to a specific detection site and detects touch, then it is possible to quantify a sensation such as the fit of a clothing item Pulse wave detector 1 may also be formed of a narrow band detector employing a polarized light filter. FIG. 17 shows one example thereof. FIG. 17(a) shows an overview of the structure of the pulse wave detector according to this modification.

As shown in this figure, pulse wave detector A is formed of a light emitting element 10a (light emitter), a light receiving element 20a (light receiver), a light polarizing plate 31a (first light polarizing means), a light polarizing plate 32a (second light polarizing means). and a filter 40a provided to the light receiving surface of the light receiving element. Pulse wave detector A is designed to radiate light on the scattering medium (blood hemoglobin) which is the detection target, and then incident this reflected light. Light polarizing plate 31a is provided to the light emitting surface of light emitting element 10a, while light polarizing plate 32a is provided to the light receiving surface of light receiving element 20a. The direction of the polarized light from these surfaces is the same. For this reason, light polarizing plates 31a,32a do not have to be separated into light emitting and light receiving sides, but may be formed of a single plate. Note that while the structure has been simplified in this figure, in actuality, light emitting element 10a and light receiving element 20a are housed in separate chambers, with the light generated from light emitting element 10a directly incidenting on light receiving element 20a.

In a pulse wave detector A having the structure described above, the light emitted by light emitting element 10a is radiated on the scattering medium after being polarized by light polarizing plate 31a. If some of this radiated light reaches the scattering medium and is absorbed, then there is also light which is reflected. Moreover, if some of this reflected light demonstrates repeated multiple scattering, then there is also light which directly approaches light receiving element 20.

Multiply scattered light, in which the light experiences repeated multiple scattering in the scattering medium, does not maintain a polarized light state when radiated. Accordingly, only a portion of this light passes through polarized light plate 32a. In contrast, light which is not multiply scattered, i.e., directly reflected light, does maintain the polarized state when radiated, so that most of it passes through light polarizing plate 32a.

Accordingly, the majority of light which passes through light polarizing plate 32a and incidents on light receiving element 20a is a directly reflected light component which does not is not multiply scattered in the scattering medium.

Figure 18A:
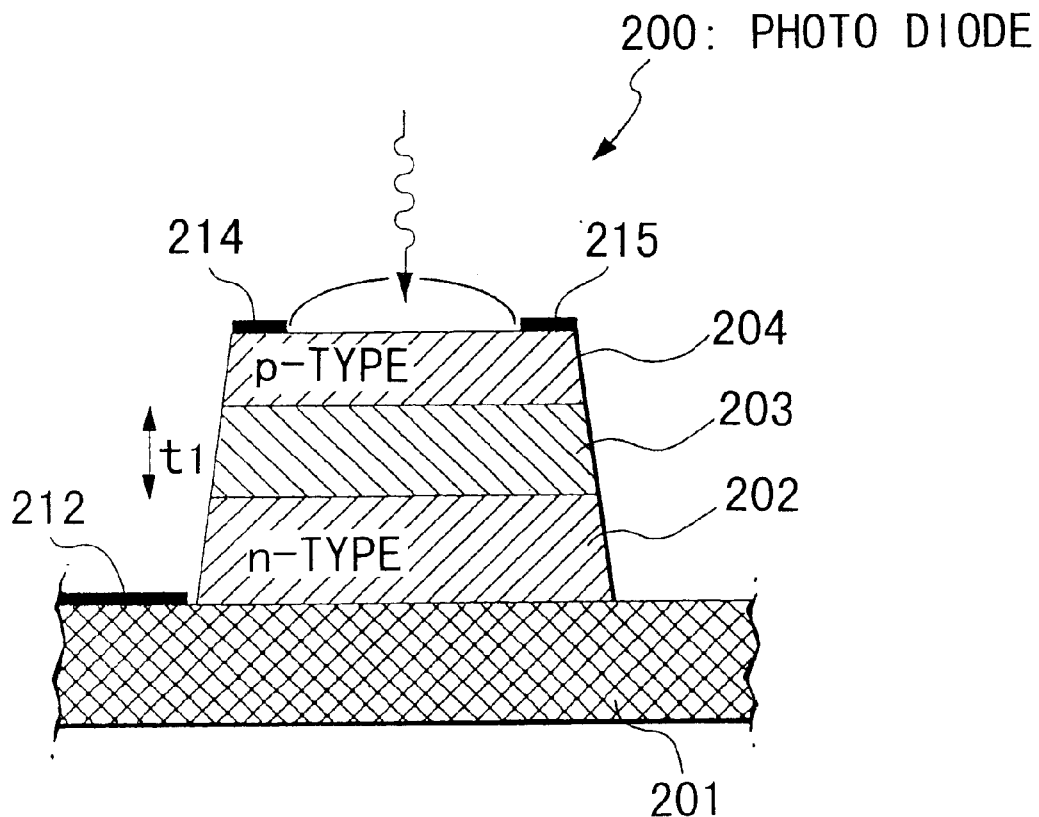
FIG. 18(a) is a cross-sectional view from the side showing the optimal structure of a photo diode employed as a light receiving element according to a modification of the present invention.

Light receiving element 20a will now be explained. FIG. 18 is a cross-sectional view from the side showing the structure of an optimal photo diode 200 employed for light receiving element 20a. As shown in this figure, photo diode 200 is formed by successively laminating a n-type layer lower mirror 202, a depletion layer 203, and a p-type layer upper mirror 204 onto a substrate (wafer) 201, and is designed to have a light resonator (light resonating member) consisting of lower mirror 202 and upper mirror 204. The resonance wavelength λr of this light resonator is determined from the following formula based on the interval of space between lower mirror 202 and upper mirror 204, i.e., the thickness $t_1$ of the depletion layer, and the index of refraction n of the depletion layer.

$$\lambda_r = 2n \cdot t_1/m$$

In this formula, an integer of 1 or greater is employed for m. However, the design typically employs an m value of 1 or 2 so that a large interval between resonance wavelengths can be achieved.

Figure 18B:
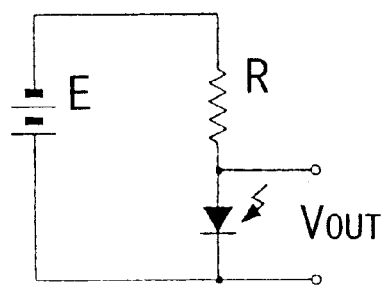
FIG. 18(b) is an electrical circuit for extracting an output.

Electrode 212 is formed on the lower layer of lower mirror 202 and electrode 214 is formed on the upper layer of upper mirror 204. As shown in FIG. 18(b), a DC electrical source E and a resistor R are connected in series to both electrodes and backward biased. An opening 215 is provided to upper mirror 204. Light reflected by the scattering medium incidents on opening 215. The incidented light is amplified due to the excitation of light traveling within the light resonator and generates a conduction electron-hole pair. Accordingly, a current proportional to the quantity of light reaching depletion layer 203 flows from lower mirror 202 to upper mirror 204. Thus, by extracting the voltage between electrodes 212 and 214 as output signal Vout, the quantity of light received at photo diode 200 can be detected.

It is ideal if lower mirror 202 and upper mirror 204 have high reflection coefficients over the entire wavelength region. However, obtaining such reflection characteristics is difficult as a practical problem. Therefore, these embodiments are designed so that the reflection coefficient is high in a band of a specific width that includes the resonance wavelength of the resonator.

For this reason, upper mirror 204 is formed by alternately laminating a material having a high detraction coefficient and a material having a low reflection coefficient. The wavelength region having a high reflection coefficient is determined by the difference between the reflection coefficients of the laminating materials. The larger this difference, the wider the band. Thus, it is preferable that the material employed for upper mirror 204 be a combination of materials that have a large difference in reflection ratios. For example, when employing an AlGaAs-type semiconductor, the upper mirror may be formed by laminating a material which changes the ratio of Al and Ga. Note that the same structure applies for lower mirror 202. Further, by combining with filter 40a, light in a narrow band can be received.

Light emitting element 10a will now be explained. The present invention is designed so that the wavelength of the light employed is selected by filter 40a and light receiving element 20a. Thus, light emitting element 10a is acceptable provided that it generates light that includes the wavelength $\lambda_r$ which is ultimately detected by light receiving element 20a. Accordingly, a regular light emitting diode may be employed for light emitting element 10a. More preferable, however, is a planar emission semiconductor laser such as explained next.

Figure 19:
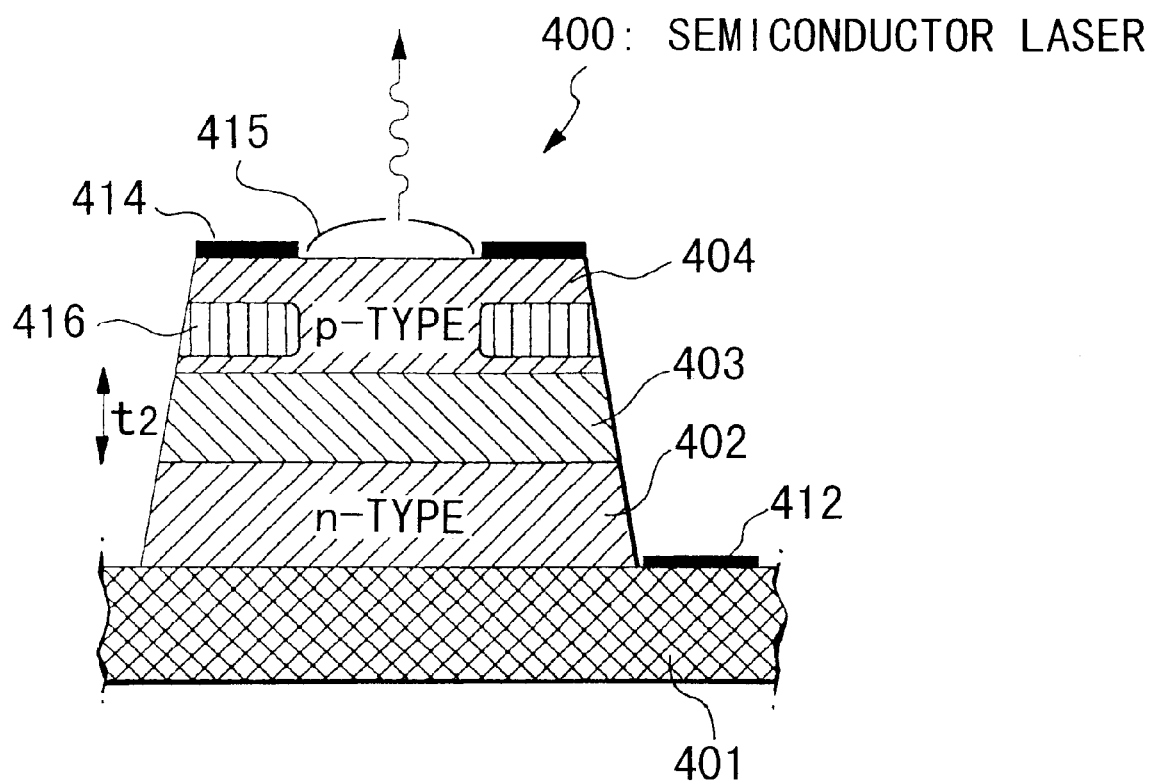
FIG. 19 is a cross-sectional view from the side showing the optimal structure of a semiconductor laser employed as a light emitting element according to a modification of the present invention.

FIG. 19 is a cross-sectional view from the side showing the structure of an optimal planar emission semiconductor laser 400 employed for light emitting element 10a. As shown in this figure, planar emission semiconductor laser 400 is formed by sequentially laminating a n-type layer lower mirror 402, active layer 403, and p-type layer upper mirror 404 onto a substrate (wafer) 401. Planar emission semiconductor laser 400 has one type of light resonator consisting of lower mirror 402 and upper mirror 404. The resonance wavelength of this light resonator is determined by the interval of space between lower mirror 402 and upper mirror 404, i.e., the resonator length $t_2$. Electrode 412 is formed on the lower layer of lower mirror 402, and electrode 414 having an opening 414 is formed on the upper layer of upper mirror 404. Electrodes 412 and 414 are forward biased.

In semiconductor laser 400, when a conduction electron and a hole are injected from electrodes 412 and 414 respectively, the carriers for these continue diffusing, reaching active layer 413. It is preferable to provide a bottlenecking layer 416 here, since the carrier injected from upper electrode 404 accumulates in active layer 403 which is directly below opening 415. The conduction electron and hole that reach active layer 403 bond again, and are discharged as light. The discharged light travels within the light resonator, and induces stimulated emission when passing through active layer 413. As a result, light having a large output is closed within the light resonator, with a portion thereof passing through upper mirror 404 and being released as laser light.

It should be noted that the structure of the semiconductor laser 400 employed here is fundamentally common to the structure of photo diode 200. The oscillating wavelength and the sensitivity wavelength are both determined by the resonator length $t_2$ and the thickness $t_1$ of the depletion layer. Accordingly, if these elements are formed on the same substrate wafer, with the active and depletion layers thereof formed by the same layer growth process, then it is not only easy to select a wavelength for the employed light in a band that is not readily effected by outside light, but it is also possible to equalize the oscillating wavelength and the sensitivity wavelength.

In this way, the light which has passed through light polarizing plate 32a and filter 40a to be ultimately detected by light receiving element 20a is light of wavelength $\lambda_r$, on which the effect of outside light is small, and which has a high proportion of directly reflected light components which is not multiply scattered by the scattering medium. For this reason, it becomes possible to detect only the directly reflected light components out of the light reflected by the scattering medium while reducing the influence of external light.

Note that filter 40a is employed with the objective of cutting light having a wavelength of $\lambda_1$ or less from the reflected light incidenting on the light receiving element. Thus, either light polarizing plate 32a or filter 40a may be disposed on the top surface.

When a pulse wave detector is formed as a narrow band detector in this way, a design which is not readily effected by external light becomes possible. Thus, the SN ratio of the pulse wave signal can be improved.

(2) Each of the preceding embodiments employed the DC component of the received light level as the touch indicator. However, in place of this, it is also acceptable to use the AC component of the received light level corresponding to the arterial blood component. Specifically, it is also acceptable for CPU 4 to separate the high band frequency component of the received light signal LS as an AC component, store the relationship between the AC component and the pressing force in calibration table 50, and generate a threshold value table 51 based on this. In this case, the touch sensation can be quantified without being influenced by the test subject's environment.

It is also acceptable to designate the ratio of the DC component and the AC component of the received light level as the indicator of touch sensation. In this case, the aforementioned ratio is calculated by CPU 4, the relationship between the ratio and the pressing force is stored in calibration table 50, and threshold value table 51 is generated based on this.

As stated for the AC and DC components of the received light level, it is also acceptable to combine a variety of touch indicators as suitable. Namely, any indicator is acceptable, provided that it is obtained based on the received light level.

(3) The preceding embodiments were explained based on the assumption that it was acceptable for the DC component of the received light level be a relative value, so that pressure sensor 103 need not be a precise device. However, it is also acceptable to employ a pressure sensor 103 which can measure the pressure precisely, store the relationship between the pressing force and each of the touch indicators cited above in calibration table 50 in advance, and then detect such touch information SJ as the grip force as an absolute pressure.

(4) In the preceding embodiments, calibration table 50 was referenced and threshold values were calculated to serve as the standard when generating touch information SJ. However, it is also acceptable to determine the threshold values without referencing calibration table 50. In this case, the interval between the received light level when no pressure is applied to the finger (i.e., maximum value Lmax) and the received light level when maximum pressure is applied to the finger (i.e., minimum value Lmin) is separated in response to the number of gradings required. This is then stored in threshold value table 51 as the threshold values. In this modification, grading of the touch sensation can be performed, provided that the maximum value Lmax and the minimum value Lmin for the received light level can be determined. Thus, pressure sensor 110 may be omitted. The received light level when nothing is gripped by the fingers may be detected as maximum value Lmax, while the received light level when an object is gripped by the fingers with maximum force may be detected as minimum value Lmin.

When performing a 2-value grading, the touch sensation may be detected by employing only the received light level when nothing is gripped by the fingers as the threshold value. Even in this case, it is possible to quantify such subtle touch sensations as whether or not an object is being touched.

(5) In the preceding embodiments, the DC component of the received light level was determined by CPU 4, however, it is also acceptable to provide a low pass filter between pulse wave detector 1 and A/D converter 2, and then convert that DC component into a direct digital signal. Further, when employing the AC component of the received light level as the touch indicator, a high pass filter and amp may be provided between pulse wave detector 1 and A/D converter 2. In this case, the dynamic range of A/D converter 2 is effectively applied, and an AC component with a high SN may be employed as the touch indicator.

(6) The touch detecting device explained in the first embodiment above may be applied in the amusement field. For example, it is frequently the case that a battle simulation game employs three buttons and a joystick as operators for characters, with attack patterns selected by suitably combining the operations of these operators. In this case, the touch detecting device may be employed in place of the three buttons. Specifically, the player attaches pulse wave detectors 1 to the first, second and third fingers of the right hand, and operates the joystick with the left hand. By pressing the first through third fingers of the right hand against the operating panel as the game progresses, the same effect can be achieved as in the case where depressing buttons. By carrying out 2-value grading in this case, it is possible to replace the use of buttons. However, if 5-value grading is performed, for example, then even more complicated actions can be provided to the characters, enabling the performance of superior entertainment.

(7) The touch detecting device explained in the preceding first embodiment may also be applied to an information inputting device such as a keyboard or mouse. For example, when applying the touch detecting device to a ten-key, pulse wave detectors 1 are attached to each of the fingers of the hands, 2-value grading is performed, and touch information SJ detected by each of the fingers is assigned to numerical values 0–9. In this case, since it is not necessary to search for keys, the input speed can be much improved. Moreover, since the user is not subjected to the key weight, it is possible to avoid such undesirable effects as tendentious which accompany key inputting operations.

Conventionally known computer keyboards include JIS or ASCII arrays. However, the number of keys employed in these exceeds 10. For this reason, touch information SJ from the fingers, on both hands alone is not sufficient. Rather, this may be supplemented by simultaneously applying pressure to a plurality of fingers. For example, a sheet-shaped key board divided into five regions may be employed in combination with the touch detecting device. Since the keyboard itself becomes unnecessary in this case, a decrease in the size of the device may be anticipated.

A mouse is typically formed of two buttons. However, it is acceptable to employ the touch detecting device in place of these buttons.

The touch detecting device may also be applied in the evaluation and design support of products employed by gripping, or in the diagnosis and rehabilitation of hand and finger function in an individual who has an impairment in this area. The touch detecting device may also be applied as a finger check for a typist.

(8) The touch transmission system explained in the second embodiment above may employ a second touch detecting device along with a pressure means which applies a mechanical action on the hand. In this case, second personal computer PC2 compares touch information SJa supplied from the outside and touch information SJb detected by second touch detecting device B, and then applies pressure on the fingers (detection site) by controlling the pressure means so that touch information SJa and touch information SJb are equal.

This may then be applied to the pulse diagnostic device explained in the third embodiment to form a pulse diagnostic information transmission system. In this case, touch information SJ in response to the received light signal is generated when the patient himself attaches pulse wave detector 1 to the finger and performs a pulse diagnosis. This touch information SJ is supplied as pulse diagnostic information from the first personal computer PC1 shown in FIG. 8 via network NET to the second personal computer where the physician is located. Then, second personal computer PC2 compares pulse diagnostic information supplied from the outside (touch information SJa) and touch information SJb detected by second touch detecting device B, and applies force on the physician's finger (detection site) by controlling the pressure means so that touch information SJa and touch information SJb are equal. This then enables the physician to know the patient's pulse. It is also acceptable in this case that the patient himself does not carry out the pulse diagnosis, but rather that the caregiver perform the pulse diagnosis by attaching pulse wave detectors 1 to his fingertips. Accordingly, this permits home care to be administered.

In the touch transmission system according to the second embodiment, infrared was employed to carry out communications between first personal computer PC1 and first touch detecting device A, and between second personal computer PC2 and second touch detecting device B. However, the present invention is not limited thereto. For example, communication may also be carried out using radio waves. Namely, any communications method may be employed, provided that it is one which does not interfere with gripping of an object by the individual.

(9) Touch information from a skilled physician was stored in ROM 6 in the preceding third embodiment. However, it is also acceptable that the physician perform a pulse diagnosis when examining the patient by applying pressure on the skin over the radius artery so as to obtain a suitable pulse phenomenon, with the touch information at this time stored in data register 52. Subsequently, the student performs a pulse diagnosis on the same patient using pulse wave detector 1, adjusting the degree of pressure in accordance with the bar graphs shown on LCD 108. Since the student is able to receive advice relating to the pulse categories, i.e., violent, smooth and normal, from a skilled physician, he is able to learn the degree of subtle pressure applied and how the pulse is registered.

(10) In the third embodiment, grading may be performed in three stages corresponding to hua, tyu and xuan, with the characters "hua, tyu and xuan" displayed on LCD 108. The pulse diagnostic information may also be displayed using bar graphs of differing lengths or numbered 1,2,3 corresponding to the "hua, tyu and xuan" characters. In this case, CPU 4 functions as a pulse diagnostic information generating means for generating pulse diagnostic information by grading touch information SJ based on threshold values P1,P2 (standard touch information) that is stored in ROM 6.

The third embodiment notified the user of the degree of pressure when the user (third party) was diagnosing a patient (test subject). However, it is also acceptable to notify the patient by employing a display in place of LCD 108. Of course, it is also acceptable for the user himself to measure his (test subject's) own pulse.

(11) The third embodiment detected the degree of pressure in the pulse diagnosis using touch information SJ, and specified the pulse phenomenon. i.e. hua-mai or xuan-mai pulse, according to this detection. However, the present invention is not limited thereto. Rather, any device may be suitably employed, provided that it is one that performs a pulse diagnosis based on touch information SJ. Touch information SJ expresses the reactive force registered at the fingertips where pulse wave detectors 1 are attached. Thus, the touch information SJ is the result when the touch sensation registered at the physician's fingertips is quantified. Accordingly, by analyzing touch information SJ, the state of the pulse can be detected. For example, the AC component of touch information SJ is the patient's pulse waveform. Therefore, by analyzing the pulse waveform, the pulse phenomenon, i.e., violent, normal or smooth, can be specified, and the state of physiological health diagnosed.

In addition, when calculating touch information SJ in the third embodiment, pressure sensor 110 shown in FIG. 5 was employed to generate calibration table 50, and threshold value table 51 was generated based on this. However, as explained in modification (4), it is of course also acceptable to generate touch information SJ without employing pressure sensor 110 or calibration table 50. In this case, the degree of pressure by the individual performing the pulse diagnosis, i.e., the hua, tyu, or xuan states when no pressure is applied, can be graded using the DC component of the pulse wave signal at the time when the individual taking the measurements decides that pressure.

Note that modifications (2) and (3) may also be applied in the third embodiment.

(12) In the preceding embodiments, touch information SJ is generated by employing threshold values to grade the received light signal detected by pulse wave detectors 1. However, since touch information SJ shows the degree of pressure, grading is not necessary as long as touch information SJ is proportional to the quantity of received light indicated by the received light signal. Namely, it is acceptable if touch information SJ is generated based on the received light signal.

The preceding embodiments employed an LCD as a notifying means relying on the visual senses. However, the notifying means in the present invention is not limited thereto. Rather, any notifying means may be employed, provided that it can notify the user of touch information SJ by relying on the five senses of hearing, smell, touch, etc.

For example, in the case of a notifying means which relies on hearing, the user may be notified of the touch information by means of a voice or sound. Thus, a device may be provided which can be used by a visually impaired person. When grading touch information SJ in five stages, if the current touch information SJ is degree 3, for example, then a voice message which states "degree of pressure 3" may be played via a speaker or earphone.

What is claimed is:

1. A touch detecting device comprising:

detecting means for receiving reflected light obtained when a detection site on the body is irradiated with light, and detecting this received light signal;

threshold value calculating means for calculating the threshold values, which can be used for grading the received light signal, based on the light signal received when there is no pressure being applied at the detection site;

threshold value table for storing the threshold values; and touch information generating means for comparing the received light signal and the respective threshold values, and generating touch information in which the touch sensation at the detection site has been quantified based on grading of the received light signal.

2. A touch detecting device comprising:

detecting means for receiving reflected light obtained when the detection site on the body is irradiated with light, and detecting this received light signal;

threshold value calculating means for calculating the threshold values, which can be used for grading the received light signal, based on the light signal received when there is no pressure being applied at the detection site and based on the light signal received when maximal pressure is being applied at the detection site;

threshold value table for storing the threshold values; and touch information generating means for comparing the received light signal and the respective threshold values, and generating touch information in which the touch sensation at the detection site has been quantified based on grading of the received light signal.

3. A touch detecting device comprising:

detecting means for receiving reflected light obtained when the detection site on the body is irradiated with light, and detecting this received light signal:

calibration table for storing in advance the relationship between the received light signal and the pressure applied at the detection site;

threshold value calculating means for associating the light signal received when no pressure is applied at the detection site and the light signal received when maximal pressure is applied at the detection site, to the relationship stored in the calibration table between the received light signals and the pressure applied at the detection site, thereby calculating threshold values which can be used for grading the received light signal;

threshold value table for storing the threshold values; and touch information generating means for comparing the received light signal and the respective threshold values, and generating touch information in which the touch sensation at the detection site has been quantified based on grading of the received light signal.

4. A touch detecting device according to one of claims 1 through 3, wherein:

the threshold value calculating means calculates the threshold values, which can be used for grading the received light signal, based on the DC level of the received light signal; and the touch information generating means compares the DC level of the received light signal and the respective threshold values, and generates touch information in which the touch sensation at the detection site has been quantified based on grading of the received light signal.

5. A touch detecting device according to one of claims 1 through 3, wherein:

the threshold value calculating means calculates threshold values, which can be used for grading the received light signal, based on the amplitude level of the received light signal; and the touch information generating means compares the amplitude level of the received light signal and the respective threshold values, and generates touch information in which the touch sensation at the detection site has been quantified based on grading of the received light signal.

6. A touch detecting device according to one of claims 1 through 3, wherein:

the threshold value calculating means calculates threshold values, which can be used for grading the received light signal, based on the ratio of the DC level and amplitude level of the received light signal; and the touch information generating means compares the threshold values with the ratio of the DC level and the amplitude level of the received light signal, and generates touch information in which the touch sensation at the detection site is quantified based on grading of the received light signal.

7. A touch detecting device according to one of claims 1 through 3, wherein the detecting means irradiates the detection site on the body with light having a wavelength in the range of 300 to 700 nm, receives the reflected light, and detects the received light signal.

8. A touch detecting device according to one of claims 1 through 3, wherein the detecting means comprises:
   a light generating member for generating light;
   a first light polarizing member for polarizing light generated by the light generating member;
   a second light polarizing member for incidenting reflected light from the polarized light, and permitting passage of light components polarized in a specific direction; and
   a light receiving member for receiving the light which has passed through the second polarizing member and outputting a received light signal in response to the amount of received light.

9. A touch detecting device according to one of claims 1 through 3, wherein the detecting means comprises:
   a light generating member for generating light;
   a first light polarizing member for polarizing light generated by the light generating member;
   a second light polarizing member for incidenting reflected light from the polarized light, and permitting passage of light components polarized in a specific direction; and
   a light receiving member for incidenting the light which has passed through, the second polarizing member;
   wherein the light receiving member comprises a light resonating member for resonating incidented light and an outputting member for outputting a received light signal in response to the light resonated by the light resonating member.

10. A touch detecting device according to one of claims 1 3, wherein the detecting means is provided to the fingertip area.

11. A touch notifying device comprising:
    a touch detecting device comprising:
       detecting means for receiving reflected light obtained when a detection site on the body is irradiated with light, and detecting this received light signal;
       threshold value calculating means for calculating the threshold values, which can be used for grading the received light signal, based on the light signal received when there is no pressure being applied at the detection site;
       threshold value table for storing the threshold values; and
       touch information generating means for comparing the received light signal and the respective threshold values, and generating touch information in which the touch sensation at the detection site has been quantified based on grading of the received light signal; and
    notifying means for notifying the user of touch information generated by the touch information generating means.

12. An information inputting device comprising:
    a plurality of touch detecting means, each of said plurality of touch detecting means comprising:
       detecting means for receiving reflected light obtained when a detection site on the body is irradiated with light, and detecting this received light signal;
       threshold value calculating means for calculating the threshold values, which can be used for grading the received light signal, based on the light signal received when there is no pressure being applied at the detection site;
       threshold value table for storing the threshold values; and
       touch information generating means for comparing the received light signal and the respective threshold values, and generating touch information in which the touch sensation at the detection site has been quantified based on grading of the received light signal; and
    wherein the touch information is employed as input information.

13. A touch replicating device comprising:
    a touch detecting device comprising:
       detecting means for receiving reflected light obtained when a detection site on the body is irradiated with light, and detecting this received light signal;
       threshold value calculating means for calculating the threshold values, which can be used for grading the received light signal, based on the light signal received when there is no pressure being applied at the detection site;
       threshold value table for storing the threshold values; and
       touch information generating means for comparing the received light signal and the respective threshold values, and generating touch information in which the touch sensation at the detection site has been quantified based on grading of the received light signal; and
    notifying means for prompting the user so that the touch information supplied from the outside and the touch information generated by the touch information generating means approach one another.

14. A touch replicating device comprising:
    a touch detecting device comprising:
       detecting means for receiving reflected light obtained when a detection site on the body is irradiated with light, and detecting this received light signal;
       threshold value calculating means for calculating the threshold values, which can be used for grading the received light signal, based on the light signal received when there is no pressure being applied at the detection site;
       threshold value table for storing the threshold values; and
    touch information generating means for comparing the received light signal and the respective threshold values, and generating touch information in which the touch sensation at the detection site has been quantified based on grading of the received light signal; and
    comparing means for comparing the touch information supplied from the outside and the touch information generated by the touch information generating means; and
    pressure means for applying pressure at the detection site based on the results of the comparison by the comparing means, so that the touch information supplied from the outside and the touch information generated by the touch information generating means coincide.

15. A touch transmission system comprising:
    a transmitting side comprising:
       a touch detecting device comprising:
          detecting means for receiving reflected light obtained when a detection site on the body is irradiated with light, and detecting this received light signal;

threshold value calculating means for calculating the threshold values, which can be used for grading the received light signal, based on the light signal received when there is no pressure being applied at the detection site;
threshold value table for storing the threshold values; and
touch information generating means for comparing the received light signal and the respective threshold values, and generating touch information in which the touch sensation at the detection site has been quantified based on grading of the received light signal; and
transmitting means which carries out communication between networks, and transmits touch information detected by the touch detecting device to the network; and
a receiving side comprising:
a touch replicating device comprising:
a touch detecting comprising:
detecting means for receiving reflected light obtained when a detection site on the body is irradiated with light, and detecting this received light signal;
threshold value calculating means for calculating the threshold values, which can be used for grading the received light signal, based on the light signal received when there is no pressure being applied at the detection site;
threshold value table for storing the threshold values; and
touch information generating means for comparing the received light signal and the respective threshold values, and generating touch information in which the touch sensation at the detection site has been quantified based on grading of the received light signal; and
notifying means for prompting the user so that the touch information supplied from the outside and the touch information generated by the touch information generating means approach one another; and
receiving means which carries out communication between the networks, and outputs touch information supplied from the transmitting side as touch information supplied from the outside.

16. A pulse diagnostic device comprising:
a touch detecting device comprising:
detecting means for receiving reflected light obtained when a detection site on the body is irradiated with light, and detecting this received light signal;
threshold value calculating means for calculating the threshold values, which can be used for grading the received light signal, based on the light signal received when there is no pressure being applied at the detection site;
threshold value table for storing the threshold values; and
touch information generating means for comparing the received light signal and the respective threshold values, and generating touch information in which the touch sensation at the detection site has been quantified based on grading of the received light signal; and
pulse diagnosing means for performing pulse diagnosis based on touch information generated by the touch information generating means.

17. A pulse diagnostic device comprising:
a touch detecting device, comprising:
detecting means for receiving reflected light obtained when a detection site on the body is irradiated with light, and detecting this received light signal;
threshold value calculating means for calculating the threshold values, which can be used for grading the received light signal, based on the light signal received when there is no pressure being applied at the detection site;
threshold value table for storing the threshold values; and
touch information generating means for comparing the received light signal and the respective threshold values, and generating touch information in which the touch sensation at the detection site has been quantified based on grading of the received light signal; and
recording means for storing in advance standard touch information showing the degree of pressure during the pulse diagnosis: and
pulse diagnosing means for carrying out a pulse diagnosis based on the touch information generated by the touch information generating means and the standard touch information.

18. A pulse diagnosis training device comprising:
a touch detecting device comprising:
detecting means for receiving reflected light obtained when a detection site on the body is irradiated with light and detecting this received light signal;
threshold value calculating means for calculating the threshold values, which can be used for grading the received light signal, based on the light signal received when there is no pressure being applied at the detection site;
threshold value table for storing the threshold values; and
touch information generating means for comparing the received light signal and the respective threshold values, and generating touch information in which the touch sensation at the detection site has been quantified based on grading of the received light signal; and
recording means for storing in advance standard touch information showing the degree of pressure during the pulse diagnosis;
pulse diagnostic information generating means for generating pulse diagnostic information after grading the touch information based on the standard touch information; and
notifying means for notifying the user of the pulse diagnostic information.

19. A pulse diagnosis training device according to claim 18, wherein the notifying means notifies the user so that the touch information generated by the touch information generating means approaches the standard touch information.

20. A pulse diagnosis training device according to claim 18, wherein a test subject carries out pulse diagnosis by attaching the detecting means to his fingertips, and in that the notifying means notifies the test subject.

21. A pulse diagnosis training device according to claim 18, wherein a third party carries out pulse diagnosis by attaching the detecting means to the fingertips, and the notifying means notifies the third party.

22. A pulse diagnostic information transmission system comprises:

a transmitting side comprising:
  a touch detecting device comprising:
    detecting means for receiving reflected light obtained when a detection site on the body is irradiated with light, and detecting this received light signal;
    threshold value calculating means for calculating the threshold values, which can be used for grading the received light signal, based on the light signal received when there is no pressure being applied at the detection site;
    threshold value table for storing the threshold values; and
    touch information generating means for comparing the received light signal and the respective threshold values, and generating touch information in which the touch sensation at the detection site has been quantified based on grading of the received light signal; and
  transmitting means that carries out communications between networks and transmits touch information detected by the touch detecting device as pulse diagnostic information to the network; and
a receiving side comprising:
  a touch replicating device comprising:
    a touch detecting comprising:
      detecting means for receiving reflected light obtained when a detection site on the body is irradiated with light, and detecting this received light signal;
      threshold value calculating means for calculating the threshold values, which can be used for grading the received light signal, based on the light signal received when there is no pressure being applied at the detection site;
      threshold value table for storing the threshold values: and
      touch information generating means for comparing the received light signal and the respective threshold values, and generating touch information in which the touch sensation at the detection site has been quantified based on grading of the received light signal; and
      notifying means for prompting the user so that the touch information supplied from the outside and the touch information generated by the touch information generating means approach one another; and
    receiving means that carries out communications between networks and outputs the pulse diagnostic information from the transmitting side to the touch replicating device as touch information supplied from the outside.

23. A pulse diagnostic information transmission system comprising:
  a transmitting side comprising:
    a touch detecting device comprising:
      detecting means for receiving reflected light obtained when a detection site on the body is irradiated with light, and detecting this received light signal;
      threshold value calculating means for calculating the threshold values which can be used for grading the received light signal, based on the light signal received when there is no Pressure being applied at the detection site;
      threshold value table for storing the threshold values; and
      touch information generating means for comparing the received light signal and the respective threshold values, and generating touch information in which the touch sensation at the detection site has been quantified based on grading of the received light signal; and
    transmitting means which generates touch information based on a received light signal obtained as a result of pulse diagnosis performed by a test subject on the transmitting side who attaches a detecting means to his fingertips, and transmits this touch information to a network as pulse diagnostic information; and
  a receiving side comprising:
    a touch replicating device comprising:
      a touch detecting comprising:
        detecting means for receiving reflected light obtained when a detection site on the body is irradiated with light, and detecting this received light signal;
        threshold value calculating means for calculating the threshold values which can be used for grading the received light signal, based on the light signal received when there is no pressure being applied at the detection site;
        threshold value table for storing the threshold values; and
        touch information generating means for comparing the received light signal and the respective threshold values, and generating touch information in which the touch sensation at the detection site has been quantified based on grading of the received light signal; and
        notifying means for prompting the user so that the touch information supplied from the outside and the touch information generated by the touch information generating means approach one another; and
      receiving means which carries out communications between networks, and outputs pulse diagnostic information from the transmitting side to the touch replicating device as touch information supplied from the outside.

24. A pulse diagnostic information transmission system comprising:
  a transmitting side comprising:
    a touch detecting device comprising:
      detecting means for receiving reflected light obtained when a detection site on the body is irradiated with light, and detecting this received light signal;
      threshold value calculating means for calculating the threshold values, which can be used for grading the received light signal, based on the light signal received when there is no pressure being applied at the detection site;
      threshold value table for storing the threshold values; and
      touch information generating means for comparing the received light signal and the respective threshold values, and generating touch information in which the touch sensation at the detection site has been quantified based on grading of the received light signal; and
    transmitting means which generates touch information based on the received light signal obtained as a result of pulse diagnosis of a test subject on the transmitting side by a third party who attaches a detecting means to his fingertips, and transmits this touch information to a network as pulse diagnostic information; and a receiving side comprising:
a touch replicating device comprising:
a touch detecting comprising:
detecting means for receiving reflected light obtained when a detection site on the body is irradiated with light, and detecting this received light signal;
threshold value calculating means for calculating the threshold values, which can be used for grading the received light signal, based on the light signal received when there is no pressure being applied at the detection site;
threshold value table for storing the threshold values; and
touch information generating means for comparing the received light signal and the respective threshold values, and generating touch information in which the touch sensation at the detection site has been quantified based on grading of the received light signal; and
notifying means for prompting the user so that the touch information supplied from the outside and the touch information generated by the touch information generating means approach one another; and receiving means which carries out communications between networks, and outputs the pulse diagnostic information from the transmitting side to the touch replicating device as touch information supplied from the outside.

25. A touch detecting method for detecting a touch sensation in the body, comprising:
a step for receiving reflected light obtained when a detection site on the body is irradiated with light, and detecting a received light signal;
a step for calculating threshold values, which can be used for grading the received light signal, based on the light signal received when there is no pressure being applied at the detection site;
a step for storing threshold values in a threshold value table;
a step for comparing the received light signal and the threshold value; and
a step for generating touch information in which the touch sensation at the detection site has been quantified based on the results of the comparison.

26. A touch detecting method for detecting a touch sensation in the body, comprising:
a step for receiving reflected light obtained when a detection site on the body is irradiated with light, and detecting a received light signal;
a step for calculating threshold values, which can be used for grading the received light signal, based on the light signal received when there is no pressure being applied at the detection site and the light signal received when maximal pressure is being applied at the detection site;
a step for storing the threshold values in a threshold value table;
a step for comparing the received light signal and the threshold value readout from the threshold value table; and
a step for generating touch information in which the touch sensation at the detection site has been quantified based on the results of the comparison.

27. A touch detecting method for detecting a touch sensation in the body, comprising:
a step for receiving reflected light obtained when a detection site on the body is irradiated with light, and detecting a received light signal;
a step for storing in advance in the calibration table the relationship between the received light signal and the pressure applied at the detection site;
a step for associating the light signal received when no pressure is applied at the detection site and the light signal received when maximal pressure is applied at the detection site, to the relationship stored in the calibration table between the received light signal and the pressure applied at the detection site, thereby calculating the threshold values which can be used for grading the received light signal;
a step for storing the threshold values in the threshold value table;
a step for comparing the received light signal and the threshold values;
a step for comparing the received light signal and the threshold values readout from the threshold value table; and
a step for generating touch information in which the touch sensation at the detection site has been quantified based on the results of the comparison.

28. A touch notifying device comprising:
a touch detecting device comprising:
detecting means for receiving reflected light obtained when the detection site on the body is irradiated with light, and detecting this received light signal;
threshold value calculating means for calculating the threshold values, which can be used for grading the received light signal, based on the light signal received when there is no pressure being applied at the detection site and based on the light signal received when maximal pressure is being applied at the detection site;
threshold value table for storing the threshold values; and
touch information generating means for comparing the received light signal and the respective threshold values, and generating touch information in which the touch sensation at the detection site has been quantified based on grading of the received light signal; and
notifying means for notifying the user of touch information generated by the touch information generating means.

29. A touch notifying device comprising:
a touch detecting device comprising:
detecting means for receiving reflected light obtained when the detection site on the body is irradiated with light, and detecting this received light signal:
calibration table for storing in advance the relationship between the received light signal and the pressure applied at the detection site;
threshold value calculating means for associating the light signal received when no pressure is applied at the detection site and the light signal received when maximal pressure is applied at the detection site, to the relationship stored in the calibration table between the received light signals and the pressure applied at the detection site, thereby calculating threshold values which can be used for grading the received light signal;

threshold value table for storing the threshold values; and touch information generating means for comparing the received light signal and the respective threshold values, and generating touch information in which the touch sensation at the detection site has been quantified based on grading of the received light signal; and notifying means for notifying the user of touch information generated by the touch information generating means.

30. An information inputting device comprising:

a plurality of touch detecting means, each of said plurality of touch detecting means comprising:

detecting means for receiving reflected light obtained when the detection site on the body is irradiated with light, and detecting this received light signal;

threshold value calculating means for calculating the threshold values, which can be used for grading the received light signal, based on the light signal received when there is no pressure being applied at the detection site and based on the light signal received when maximal pressure is being applied at the detection site;

threshold value table for storing the threshold values; and touch information generating means for comparing the received light signal and the respective threshold values, and generating touch information in which the touch sensation at the detection site has been quantified based on grading of the received light signal; and wherein the touch information is employed as input information.

31. An information inputting device comprising:

a plurality of touch detecting means, each of said plurality of touch detecting means comprising:

detecting means for receiving reflected light obtained when the detection site on the body is irradiated with light, and detecting this received light signal:

calibration table for storing in advance the relationship between the received light signal and the pressure applied at the detection site;

threshold value calculating means for associating the light signal received when no pressure is applied at the detection site and the light signal received when maximal pressure is applied at the detection site, to the relationship stored in the calibration table between the received light signals and the pressure applied at the detection site, thereby calculating threshold values which can be used for grading the received light signal;

threshold value table for storing the threshold values; and touch information generating means for comparing the received light signal and the respective threshold values, and generating touch information in which the touch sensation at the detection site has been quantified based on grading of the received light signal; and wherein the touch information is employed as input information.

32. A touch replicating device comprising:

a touch detecting comprising:

detecting means for receiving reflected light obtained when the detection site on the body is irradiated with light, and detecting this received light signal;

threshold value calculating means for calculating the threshold values, which can be used for grading the received light signal, based on the light signal received when there is no pressure being applied at the detection site and based on the light signal received when maximal pressure is being applied at the detection site;

threshold value table for storing the threshold values; and touch information generating means for comparing the received light signal and the respective threshold values, and generating touch information in which the touch sensation at the detection site has been quantified based on grading of the received light signal; and notifying means for prompting the user so that the touch information supplied from the outside and the touch information generated by the touch information generating means approach one another.

33. A touch replicating device comprising:

a touch detecting comprising:

detecting means for receiving reflected light obtained when the detection site on the body is irradiated with light, and detecting this received light signal:

calibration table for storing in advance the relationship between the received light signal and the pressure applied at the detection site;

threshold value calculating means for associating the light signal received when no pressure is applied at the detection site and the light signal received when maximal pressure is applied at the detection site, to the relationship stored in the calibration table between the received light signals and the pressure applied at the detection site, thereby calculating threshold values which can be used for grading the received light signal;

threshold value table for storing the threshold values; and touch information generating means for comparing the received light signal and the respective threshold values, and generating touch information in which the touch sensation at the detection site has been quantified based on grading of the received light signal; and notifying means for prompting the user so that the touch information supplied from the outside and the touch information generated by the touch information generating means approach one another.

34. A touch replicating device comprising:

a touch detecting device comprising:

detecting means for receiving reflected light obtained when the detection site on the body is irradiated with light, and detecting this received light signal;

threshold value calculating means for calculating the threshold values, which can be used for grading the received light signal, based on the light signal received when there is no pressure being applied at the detection site and based on the light signal received when maximal pressure is being applied at the detection site;

threshold value table for storing the threshold values; and touch information generating means for comparing the received light signal and the respective threshold values, and generating touch information in which the touch sensation at the detection site has been quantified based on grading of the received light signal; and comparing means for comparing the touch information supplied from the outside and the touch information generated by the touch information generating means; and pressure means for applying pressure at the detection site based on the results of the comparison by the comparing means, so that the touch information supplied from the outside and the touch information generated by the touch information generating means coincide.

35. A touch replicating device comprising:

a touch detecting device comprising:

detecting means for receiving reflected light obtained when the detection site on the body is irradiated with light, and detecting this received light signal:

calibration table for storing in advance the relationship between the received light signal and the pressure applied at the detection site;

threshold value calculating means for associating the light signal received when no pressure is applied at the detection site and the light signal received when maximal pressure is applied at the detection site, to the relationship stored in the calibration table between the received light signals and the pressure applied at the detection site, thereby calculating threshold values which can be used for grading the received light signal;

threshold value table for storing the threshold values; and touch information generating means for comparing the received light signal and the respective threshold values, and generating touch information in which the touch sensation at the detection site has been quantified based on grading of the received light signal; and comparing means for comparing the touch information supplied from the outside and the touch information generated by the touch information generating means; and pressure means for applying pressure at the detection site based on the results of the comparison by the comparing means, so that the touch information supplied from the outside and the touch information generated by the touch information generating means coincide.

* * * * *

UNITED STATES PATENT AND TRADEMARK OFFICE
CERTIFICATE OF CORRECTION

PATENT NO. : 6,162,185
DATED : December 19, 2000
INVENTOR(S) : Kazuhiko Amano et al.

Page 1 of 1

It is certified that error appears in the above-identified patent and that said Letters Patent is hereby corrected as shown below:

Column 27,
Line 33, insert -- through -- after "claims 1".

Column 31,
Line 37, change ":" to -- ; -- after "values".
Line 65, change "Pressure" to -- pressure --.

Signed and Sealed this

Nineteenth Day of February, 2002

Attest:

Attesting Officer

JAMES E. ROGAN
*Director of the United States Patent and Trademark Office*